United States Patent
Jones et al.

(10) Patent No.: US 10,595,732 B2
(45) Date of Patent: Mar. 24, 2020

(54) PULSE WAVE DETECTION DEVICE AND PULSE WAVE DETECTION PROGRAM

(71) Applicant: EQUOS RESEARCH CO., LTD., Tokyo (JP)

(72) Inventors: Michael Jones, Tokyo (JP); Hideo Yamada, Tokyo (JP)

(73) Assignee: EQUOS RESEARCH CO., LTD., Tokyo (JP)

( * ) Notice: Subject to any disclaimer, the term of this patent is extended or adjusted under 35 U.S.C. 154(b) by 0 days.

(21) Appl. No.: 15/563,409

(22) PCT Filed: Mar. 30, 2016

(86) PCT No.: PCT/JP2016/060508
§ 371 (c)(1),
(2) Date: Sep. 29, 2017

(87) PCT Pub. No.: WO2016/159151
PCT Pub. Date: Oct. 6, 2016

(65) Prior Publication Data
US 2018/0085010 A1    Mar. 29, 2018

(30) Foreign Application Priority Data

Mar. 31, 2015 (JP) .................. 2015-073964

(51) Int. Cl.
*A61B 5/021* (2006.01)
*G06T 7/90* (2017.01)
(Continued)

(52) U.S. Cl.
CPC ........ *A61B 5/02108* (2013.01); *G06T 1/0007* (2013.01); *G06T 7/20* (2013.01);
(Continued)

(58) Field of Classification Search
CPC ..... A61B 5/02108; A61B 5/00; A61B 5/0245; G06T 7/90; G06T 7/20; G06T 1/0007; H04N 5/57; H04N 5/2316
(Continued)

(56) References Cited

U.S. PATENT DOCUMENTS

2004/0015098 A1*  1/2004  Souvestre .............. A61B 3/113
                                                        600/558
2005/0152613 A1   7/2005  Okutsu et al.
(Continued)

FOREIGN PATENT DOCUMENTS

CN         1641699 A      7/2005
CN       104364798 A      2/2015
(Continued)

OTHER PUBLICATIONS

Ming-Zher Poh, Daniel J. McDuff and Rosalind W. Picard. "Advancements in Noncontact, Multiparameter Physiological Measurements Using a Webcam". IEEE Transactions on Biomedical Engineering, vol. 58, No. 1 (2011), pp. 7-11.
(Continued)

*Primary Examiner* — Jefferey F Harold
*Assistant Examiner* — Omer Khalid
(74) *Attorney, Agent, or Firm* — Oliff PLC

(57) ABSTRACT

A pulse wave detection device color converts a frame image of a moving image from RBG components to YIQ components, and identifies an eye section using the eye color of a user prepared in advance with a Q component. Next, the pulse wave detection device uses the Y values of the eye section to detect the brightness of the imaging environment. Then, the pulse wave detection device detects a pulse wave signal Qm on the basis of the average of the Q-values of a skin section in the frame image, corrects a change in the brightness by subtracting from Qm the average value Ye of
(Continued)

the Y values of the eye section, and thereby outputs a post-brightness-correction Qm. As a result, a pulse wave can be successfully detected even if the brightness is changing because the user is moving in a vehicle or the like.

13 Claims, 16 Drawing Sheets

(51) Int. Cl.
  *G06T 1/00* (2006.01)
  *G06T 7/20* (2017.01)
  *H04N 5/232* (2006.01)
  *H04N 5/57* (2006.01)

(52) U.S. Cl.
  CPC ........... *G06T 7/90* (2017.01); *H04N 5/23216* (2013.01); *H04N 5/57* (2013.01); *G06T 2207/30041* (2013.01); *G06T 2207/30201* (2013.01)

(58) Field of Classification Search
  USPC ........................................................ 382/103
  See application file for complete search history.

(56) References Cited

U.S. PATENT DOCUMENTS

| | | | |
|---|---|---|---|
| 2006/0141466 A1* | 6/2006 | Pinet | G01N 21/23 435/6.11 |
| 2007/0025722 A1* | 2/2007 | Matsugu | G03B 17/16 396/263 |
| 2009/0157482 A1* | 6/2009 | Jung | A61B 5/04842 705/7.33 |
| 2014/0079295 A1 | 3/2014 | Yoon et al. | |
| 2014/0086462 A1 | 3/2014 | Shan et al. | |
| 2014/0153800 A1 | 6/2014 | Kirenko et al. | |
| 2016/0228011 A1* | 8/2016 | Tsubaki | A61B 5/0077 |
| 2017/0277950 A1* | 9/2017 | Sung | G06K 9/00 |

FOREIGN PATENT DOCUMENTS

| | | |
|---|---|---|
| EP | 2 893 872 A1 | 7/2015 |
| JP | 2003-348614 A | 12/2003 |
| JP | 2007-096379 A | 4/2007 |
| JP | 2009-072438 A | 4/2009 |
| JP | 2009-213637 A | 9/2009 |
| JP | 2009-252243 A | 10/2009 |
| JP | 2010-239499 A | 10/2010 |
| JP | 2014-198201 A | 10/2014 |
| JP | 2014-198202 A | 10/2014 |
| JP | 2014-206785 A | 10/2014 |
| WO | 2014/004179 A1 | 1/2014 |
| WO | 2014/038077 A1 | 3/2014 |

OTHER PUBLICATIONS

Jun. 21, 2016 Search Report Issued in International Application No. PCT/JP2016/060507.
Oct. 3, 2017 International Preliminary Report on Patentability Issued in International Patent Application No. PCT/JP2016/060507.
U.S. Appl. No. 15/563,470, filed Sep. 29, 2017 in the name of Jones et al.
Oct. 3, 2017 International Preliminary Report on Patentability issued in International Patent Application No. PCT/JP2016/060508.
Feb. 16, 2018 Office Action issued in Japanese Patent Application No. 2015-073965.
Jul. 17, 2018 Office Action issued in Japanese Patent Application No. 2017-510146.
Mar. 1, 2019 Office Action issued in U.S. Appl. No. 15/563,470.
Dec. 11, 2018 Office Action issued in Japanese Patent Application No. 2017-510146.
Sep. 17, 2018 Extended Search Report issued in European Patent Application No. 16773031.6.
Kakumanu et al. "A Survey of Skin-Color Modeling and Detection Methods". Pattern Recognition, vol. 40, pp. 1106-1122, Nov. 6, 2006.
Sahindrakar, Pratik. "Improving Motion Robustness of Contact-Less Monitoring of Heart Rate Using Video Analysis". Technische Universiteit Eindhoven University of Technology; Aug. 24, 2011.
Sep. 18, 2018 Extended Search Report issued in European Patent Application No. 16773032.4.
Nov. 1, 2019 Office Action issued in Chinese Patent Application No. 201680019452.1.
Zhengjie Wan, "Research of Heart Rate Detection Based on Facial Video", Chinese Master's Theses Full-text Database Information Science and Technology, I138-2103 (Mar. 15, 2015).
Nov. 1, 2019 Office Action dated in Chinese Patent Application No. 201680019574.0.

* cited by examiner

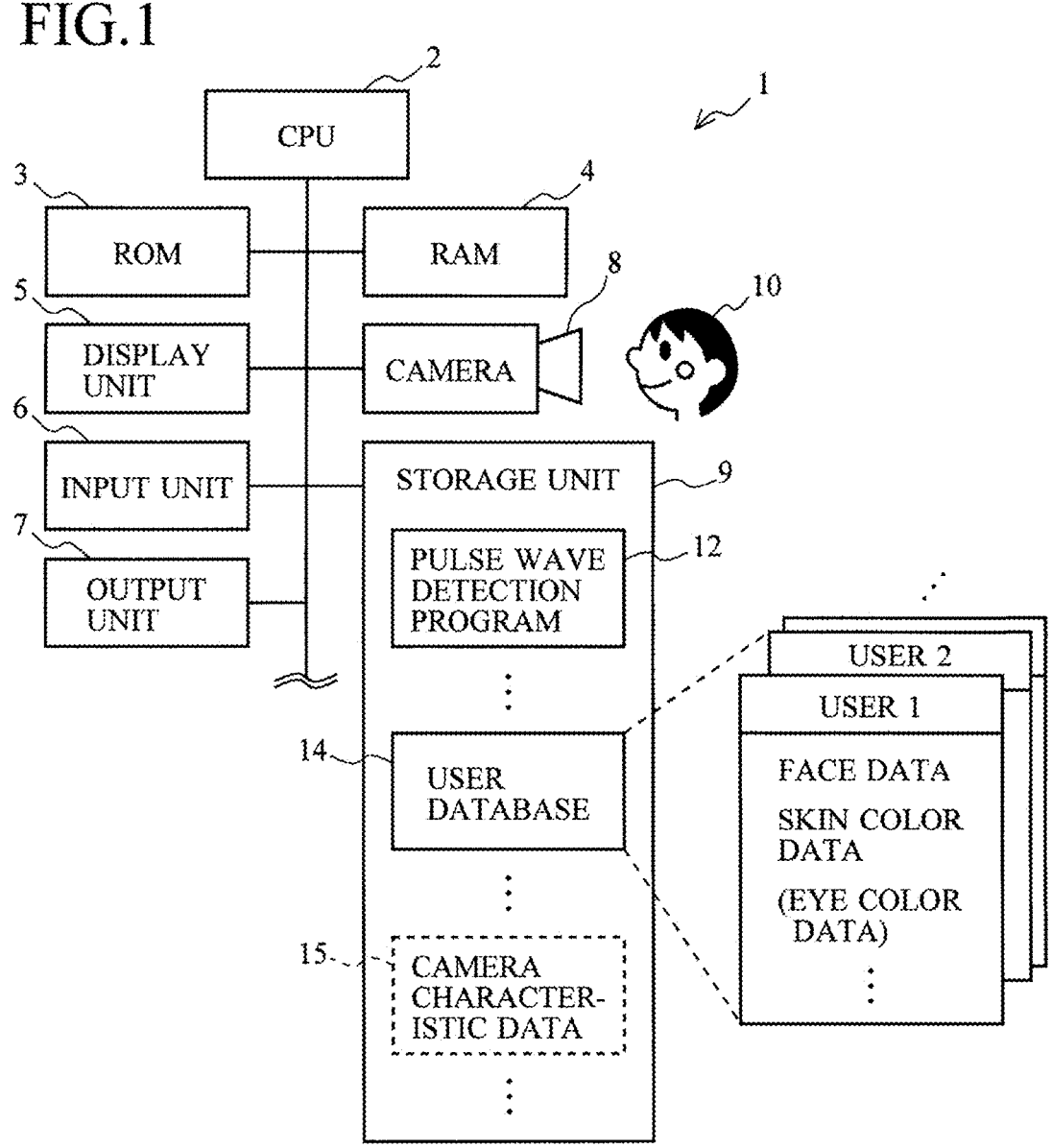

RGB SPACE

HSV SPACE

YIQ SPACE

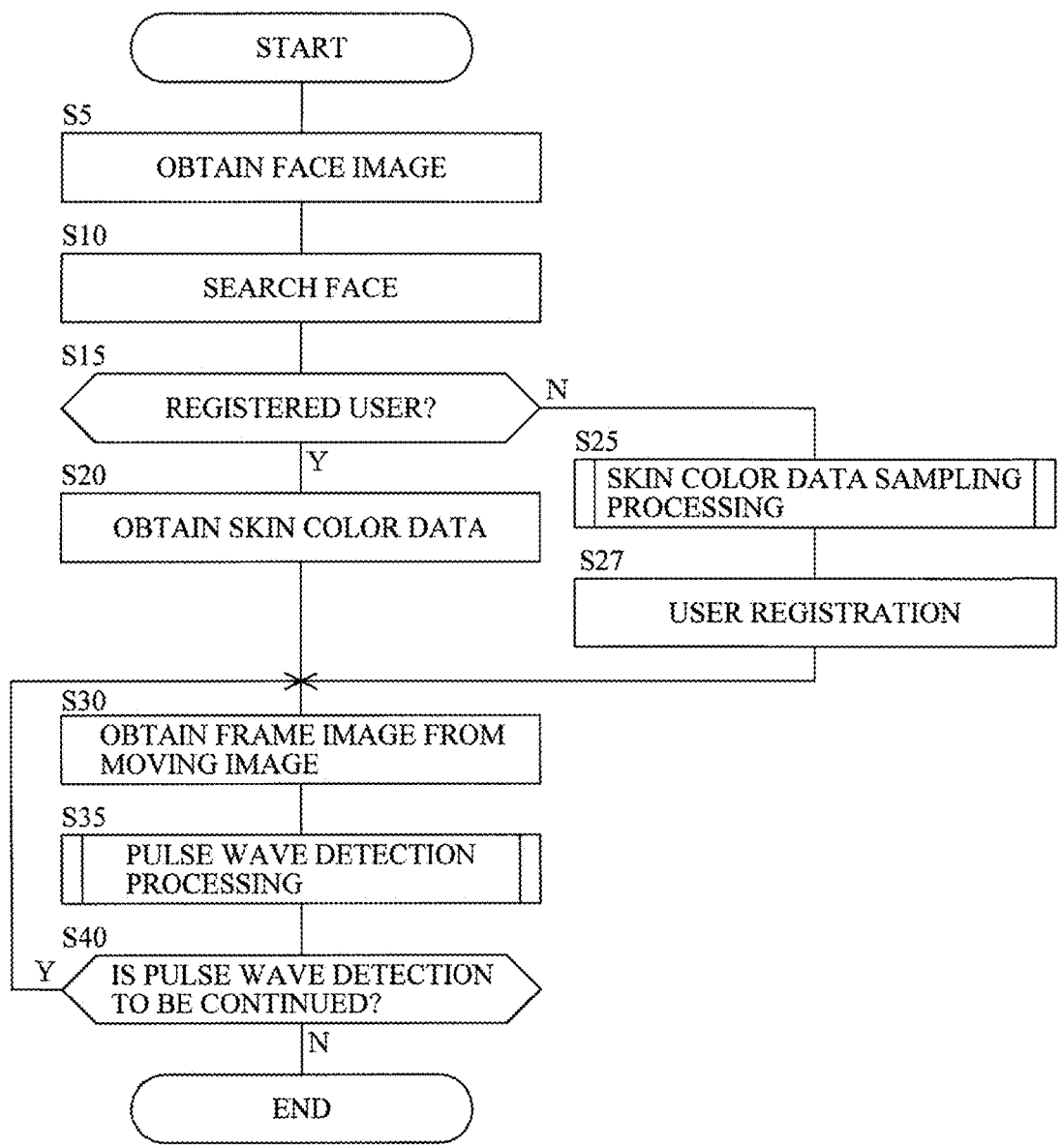

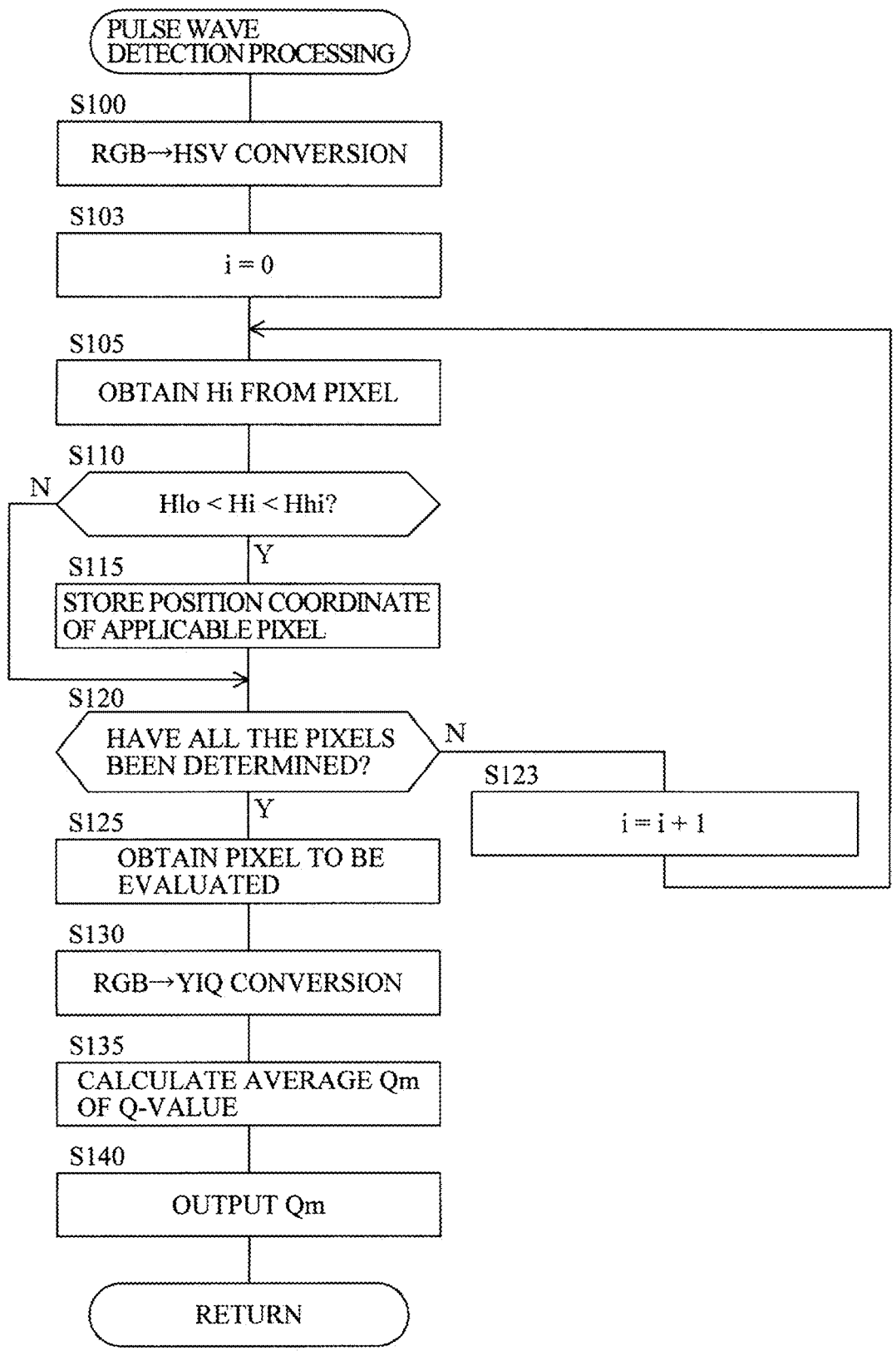

FIG.8(a)
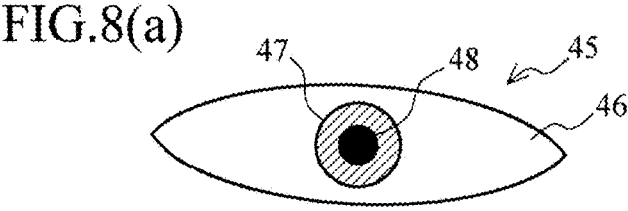
FIG.8(b)
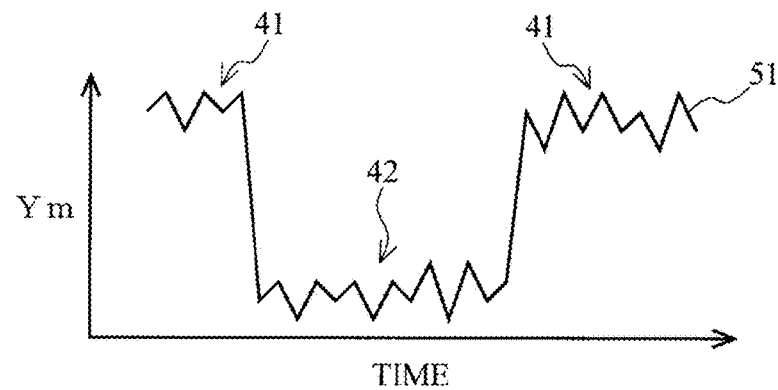
FIG.8(c) BEFORE CORRECTION Qm
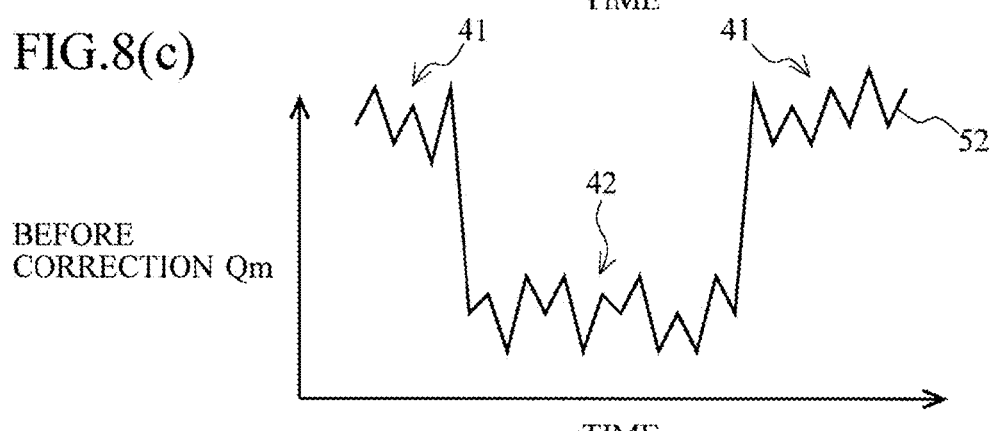
FIG.8(d) AFTER CORRECTION Qm
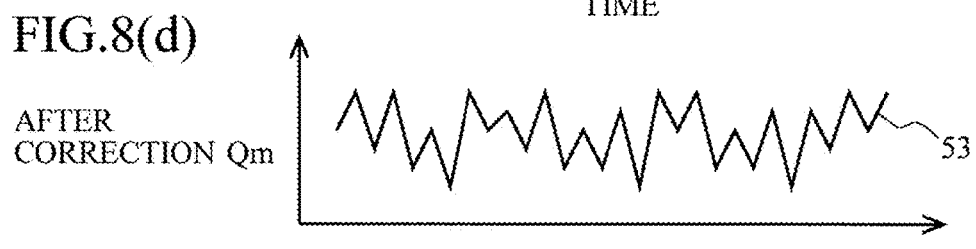
FIG.8(e)
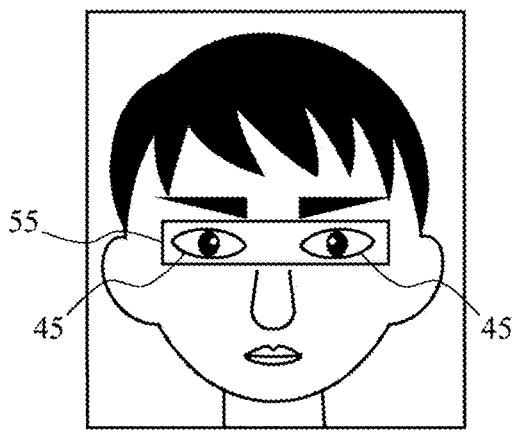
FIG.8(f)
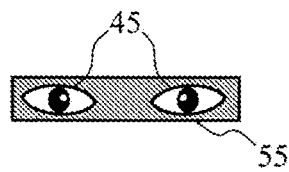

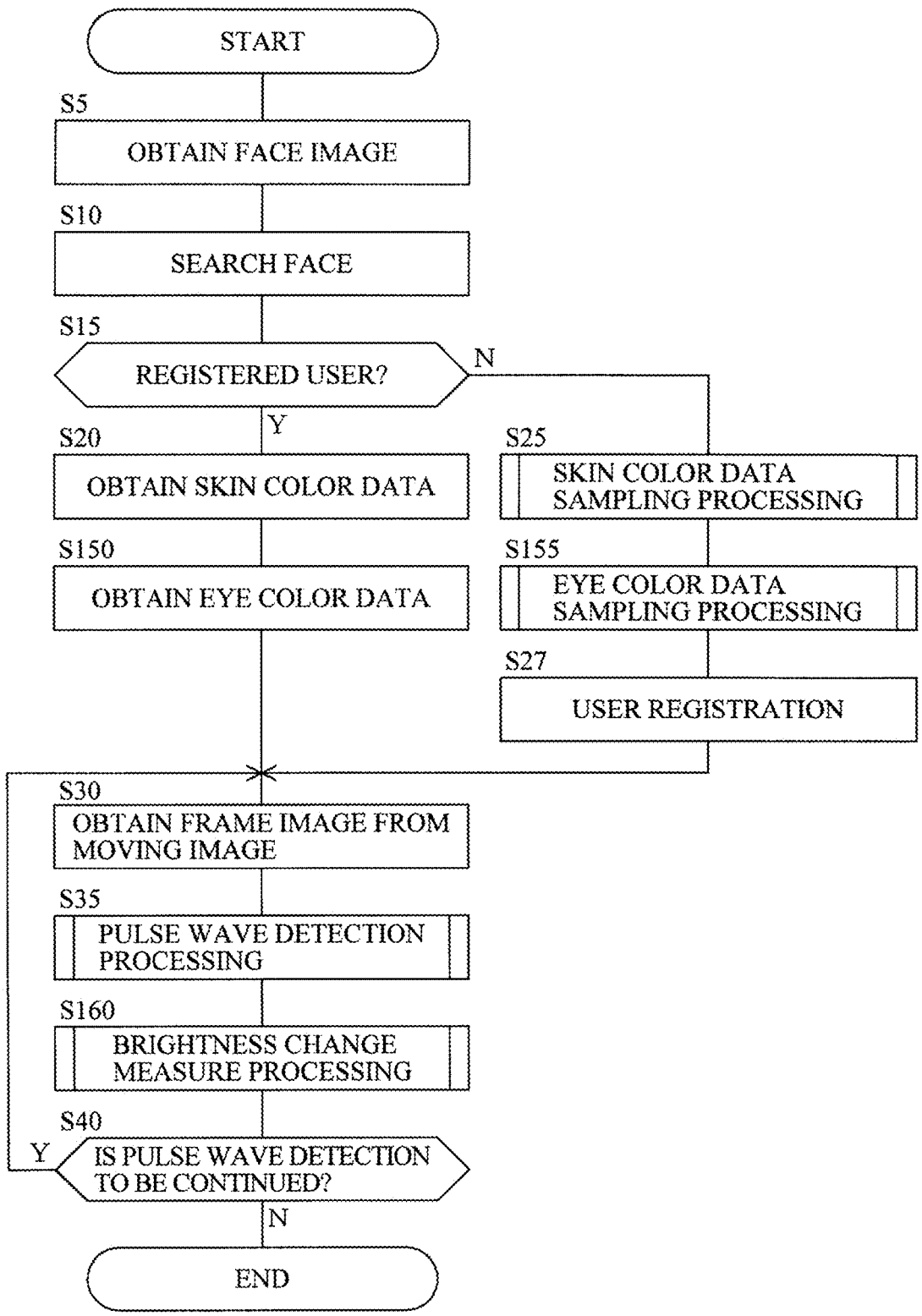

PULSE WAVE DETECTION DEVICE AND PULSE WAVE DETECTION PROGRAM

TECHNICAL FIELD

The present invention relates to a pulse wave detection device and a pulse wave detection program and relates to those detecting a pulse wave by using image processing, for example.

BACKGROUND ART

Detection of a pulse wave is extremely important in understanding a physiological state of a human being and a technology for detecting this from a remote place in a non-contact manner is in demand.

Such technologies include a study made by Massachusetts Institute of Technology which is a non-patent literature.

This technology detects a pulse wave by taking a moving image of the face of a subject by a web camera and analyzing the moving image by a laptop computer after the photographing (that is, not by real-time processing but by processing later).

This study realizes non-contact detection of a pulse wave by using an inexpensive general purpose device and a simple method against conventional detection of the pulse wave by using a special expensive device such as a laser and Doppler radar.

Here, an outline of this technology will be described by using FIG. 16.

First, as illustrated in FIG. 16(a), an evaluation region 101 having a rectangular shape is set on a screen of the moving image, the subject is seated so that the face of the subject is contained in the evaluation region 101, and the face in a still state is photographed in a moving image. The experiment is conducted indoors, and sunlight incident through a window is used as a light source.

By separating the obtained moving image into each of an R component, a G component, and a B component and averaging them, fluctuations on which the pulse waves is superimposed are obtained as illustrated in FIG. 16(b).

Each of these components include a pulse wave signal weighted in accordance with a light absorbing characteristic of hemoglobin or the like, and the pulse wave is obtained by conducting ICA (Independent Component Analysis) or the like on it.

The pulse wave is obtained from the moving image as above because, since a volume of a blood vessel is changed in accordance with heartbeats of the subject, an optical distance that the sunlight is transmitted through the skin is changed, and it appears as a change in reflected light from the face.

However, this technology is performed under an ideal environment of a laboratory, and there has been a problem that use in a practical scene such as detection of the pulse wave of a driver by mounting a pulse wave detection device on a vehicle, for example, there is a problem that a change in brightness becomes a disturbance element and makes detection of a pulse difficult.

CITATION LIST

Non-Patent Literature

Non-Patent Literature 1: Advancements in Noncontact, Multiparameter Physiological Measurements Using a Webcam, Ming-Zher Poh, Daniel J. McDuff, and Rosalind W. Picard, IEEE Transactions on Biomedical Engineering, Vol. 58, No. 1, January 2011

DISCLOSURE OF THE INVENTION

Problem to be Solved by the Invention

The present invention has an object to conduct pulse wave detection with robustness against a change in brightness.

Means for Solving the Problem (1) In order to achieve above mentioned object, the invention described in claim 1 provides a pulse wave detection device comprising: moving image obtaining means for obtaining a moving image photographing a region including a face of a target, eye portion specifying means for specifying an eye portion of the target shown on the moving image, brightness change obtaining means for obtaining a change in brightness caused by a change in a photographing environment of the moving image from a change in a predetermined color space component of the specified eye portion, brightness correcting means for correcting the brightness of the moving image using the obtained change in the brightness, pulse wave obtaining means for obtaining a pulse wave of the target from a temporal change in the predetermined color space component in a skin portion of the target corrected as above; and output means for outputting the obtained pulse wave.

(2) The invention described in claim 2 provides the pulse wave detection device according to claim 1, further comprising: skin portion specifying means for specifying a skin portion of the target shown on the obtained moving image, wherein the pulse wave obtaining means obtains a pulse wave of the target from the temporal change of the predetermined color space component on the specified skin portion.

(3) The invention described in claim 3 provides the pulse wave detection device according to claim 2, further comprising: reference component registration means for registering a reference component which is a color space component to be a reference for specifying the eye portion of the target, wherein the eye portion specifying portion specifies a portion where the predetermined color space component corresponds to the registered reference component in the moving image as the eye portion.

(4) The invention described in claim 4 provides the pulse wave detection device according to claim 2 or 3, wherein the skin portion specifying means specifies a portion where the predetermined color space component corresponds to the registered reference component in the moving image as the skin portion.

(5) The invention described in claim 5 provides the pulse wave detection device according to claim 2, 3 or 4, wherein the color space component used by the brightness change obtaining means for obtaining the change in brightness, the color space component used by the pulse wave obtaining means for obtaining the pulse wave, and the color space component used by the skin portion specifying means for specifying the skin portion are different color space components.

(6) The invention described in claim 6 provides the pulse wave detection device according to claim 5, wherein the color space component used by the brightness change obtaining means for obtaining the change in brightness and the color space component used by the pulse wave obtaining means for obtaining the pulse wave are a brightness component (Y) and a chromaticity component (Q) of a YIQ color space made of the brightness component (Y) and the chromaticity components (I, Q), respectively; and the color space component used by the skin portion specifying means for specifying the skin portion is a hue component (H) of an HSV color space made of the hue component (H), a saturation component (S), and a brightness component (V).

(7) The invention described in claim 7 provides the pulse wave detection device according to any one of claims 2 to 6, further comprising: color space converting means for converting a color space, wherein the pulse wave obtaining means, the brightness change obtaining means, and the skin portion specifying means obtain a color space component in the color space obtained by converting the obtained moving image by the color space converting means.

(8) The invention described in claim 8 provides the pulse wave detection device according to claim 3, further comprising: face image obtaining means for obtaining a face image obtained by photographing the face of the target; and region specifying means for specifying a region of the eye in the face by face recognition processing in the obtained face image, wherein the reference component registration means registers a color space component in the specified region as the reference component.

(9) The invention described in claim 9 provides the pulse wave detection device according to claim 8, wherein the reference component registration means registers a value obtained by applying predetermined statistical processing to distribution of a color space component in the specified region as the reference component.

(10) The invention described in claim 10 provides the pulse wave detection device according to any one of claims 1 to 7, wherein the eye portion specifying means specifies the eye portion by the pixel values of the moving image.

(11) The invention described in claim 11 provides the pulse wave detection device according to any one of claims 1 to 10, wherein the brightness correcting means executes the correction by the pixel values of the moving image.

(12) The invention described in claim 12 provides the pulse wave detection device according to any one of claims 1 to 11, wherein the target is a passenger of transportation equipment, and monitoring means for monitoring a physical condition of the passenger by using the output pulse is provided.

(13) The invention described in claim 13 provides a pulse wave detection program for realizing by a computer: a moving image obtaining function of obtaining a moving image photographing a region including a face of a target, an eye portion specifying function of specifying an eye portion of the target shown on the moving image, a brightness change obtaining function of obtaining a change in brightness caused by a change in a photographing environment of the moving image from a change in a predetermined color space component of the specified eye portion, a brightness correcting function of correcting the brightness of the moving image using the obtained change in the brightness, a pulse wave obtaining function of obtaining a pulse wave of the target from a temporal change in the predetermined color space component in a skin portion of the target corrected as above; and an output function of outputting the obtained pulse wave.

Effect of the Invention (1) According to the invention described in claim 1, brightness of a moving image can be corrected by obtaining a change in the brightness from an eye portion of a target.

(2) According to the invention described in claim 2, the disturbance element shown on the moving image is excluded, only a skin portion is taken out, and a pulse wave can be detected therefrom and thus, accuracy of pulse wave detection can be improved.

(3) According to the invention described in claim 3, the disturbance element shown on the moving image is excluded, only the eye portion is taken out, and accuracy of brightness correction can be improved.

(4) According to the invention described in claim 4, the skin portion can be easily extracted from the moving image by comparison with a reference component.

(5) According to the invention described in claim 5, robustness against the disturbance element can be improved by employing combination of color space components suitable for an observation target (since targets to be observed by light are different in a change in brightness, skin, and a pulse wave).

(6) According to the invention described in claim 6, by combining a Y-component found to be suitable for detection of the change in brightness, an H-component found to be suitable for specification of the skin portion, and a Q-component found to be suitable for pulse wave detection, robustness against the disturbance element can be further improved.

(7) According to the invention described in claim 7, by including color space conversion processing inside a pulse wave detection device instead of an external device, the pulse wave can be detected easily on a real-time basis.

(8) According to the invention described in claim 8, by sampling a reference value of an eye color from the target himself/herself, the reference value including a fine difference of the eye color in persons can be obtained easily.

(9) According to the invention described in claim 9, biased distribution of eye colors with a large individual difference can be averaged by statistical processing, whereby reliability of a reference component can be improved.

(10) According to the invention described in claim 10, since the eye portion is extracted for each pixel instead of a region surrounded by a closed curve (also pixels not applicable to the eye portion are scattered), the pixels acting as the disturbance element can be excluded from an evaluation target, whereby detection accuracy can be improved.

(11) According to the invention described in claim 11, since the region surrounded by the closed curve can be corrected for each pixel instead of correction by a representative value, detection accuracy can be improved.

(12) According to the invention described in claim 12, a physical condition of a passenger onboard transportation equipment can be monitored.

(13) According to the invention described in claim 13, by distributing a pulse wave detection program and by installing this in a general purpose computer, a pulse wave detection device can be configured easily and inexpensively.

BRIEF DESCRIPTION OF THE DRAWINGS

FIG. 1 is a view illustrating configuration of a pulse wave detection device.

FIG. 4 is a flowchart for explaining a procedure of entire processing.

FIG. 6 is a flowchart for explaining a procedure of pulse wave detection processing.

FIG. 8 are a view for explaining a correcting method of a change in brightness.

FIG. 9 is a flowchart for explaining a procedure of entire processing in a second embodiment.

Figure 2A:
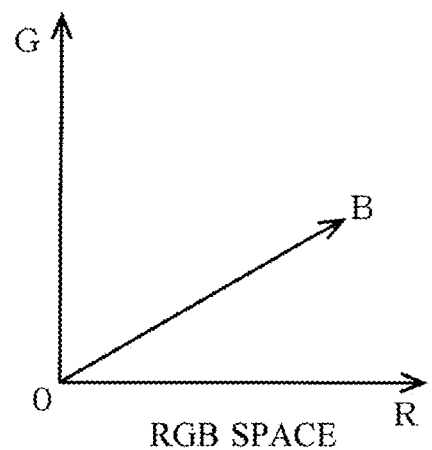
FIG. 2 are a view for explaining a color space.

DESCRIPTION OF THE EMBODIMENTS (1) Outline of Embodiments

In a first embodiment, a pulse wave detection device 1 color converts a frame image of a moving image from RGB components to HSV components and specifies a skin portion by using a skin color of a user prepared in advance with an H component. The H component is used because robustness is improved by using the H component in specification of the skin.

Subsequently, the pulse wave detection device 1 converts the skin portion of the frame image to YIQ components and takes Qm obtained by averaging a Q value of each pixel as a pulse wave signal. The Q component is used because robustness is improved by using the Q component for detection of the pulse wave signal.

The pulse wave detection device 1 obtains a chronological change of the pulse wave signal Qm by applying the processing described above to each frame image and outputs it as a pulse wave.

As described above, since the pulse wave detection device 1 can set the skin portion in the moving image to the evaluation region (ROI: Region of Interest), it can favorably detect the pulse wave by excluding the disturbance elements such as a background from pulse wave detection targets.

In a second embodiment, the pulse wave detection device 1 color converts frame image in the moving image the RGB components to the YIQ components and specifies the eye portion by using an eye color of the user prepared in advance with the Q component.

Then, the pulse wave detection device 1 detects brightness of a photographing environment with the Y value of the eye portion. Since the pulse wave signal does not appear in the eye portion, it can be used as a detection target of brightness.

Subsequently, the pulse wave detection device 1 detects the pulse wave signal Qm from an average of the Q values of the skin portion in the frame image and corrects a change of the brightness by subtracting an average value Ye of the Y values of the eye portion from this and outputs Qm after brightness correction.

As a result, even if the brightness changes since the user moves by a vehicle or the like, the pulse wave can be detected favorably.

In a third embodiment, the pulse wave detection device 1 includes camera characteristic data for correcting fluctuation in characteristics of the pixel caused by the camera characteristics. Then, the Q value of the skin portion in the frame image is corrected by the camera characteristic data.

The pulse wave detection device 1 updates the camera characteristic data by using a change in the Q value of the skin portion caused by movement of the skin portion in the image.

Moreover, the pulse wave detection device 1 limits a color as a correction target to the skin color, which makes complicated algorithm or calculation unnecessary, and a calculation load is reduced, and real-time processing of the moving image can be executed favorably.

(2) Details of Embodiments

First Embodiment

FIG. 1 is a view illustrating configuration of the pulse wave detection device 1 according to this embodiment.

The pulse wave detection device 1 is mounted on a vehicle, for example, and monitors a pulse wave of a passenger (a driver or a passenger on a seat next to the driver's) and grasps physiological states such as a physical condition or a tensed state of the driver.

Moreover, the device can be used for detecting/monitoring a pulse wave of a patient or a victim at a medical site or a disaster site.

The pulse wave detection device 1 includes a CPU (Central Processing Unit) 2, a ROM (Read Only Memory) 3, a RAM (Random Access Memory) 4, a display unit 5, an input unit 6, an output unit 7, a camera 8, a storage unit 9 and the like and detects (or estimates) the pulse wave of a user 10 (a target of pulse wave detection).

The CPU 2 is a central processing unit for executing various types of information processing or control in accordance with programs stored in the storage unit 9 or the ROM 3.

In this embodiment, a moving image taken by the camera 8 is subjected to image processing, and the pulse wave of the user 10 is detected.

The ROM 3 is a read only memory and stores basic programs and parameters for operating the pulse wave detection device 1.

The RAM 4 is a memory capable of reading/writing and provides a working memory when the CPU 2 is operated.

In this embodiment, it extends and stores a frame image (still image of one frame) constituting the moving image or stores a calculation result so as to support the CPU 2 to detect the pulse wave from a portion of the skin (hereinafter referred to as a skin portion) in a frame image.

The display unit 5 is constituted by using a display device such as a liquid crystal screen and displays information required for operation of the pulse wave detection device 1 such as an operation screen of the pulse wave detection device 1 or display of a pulse wave.

The input unit 6 is constituted by using an input device such as a touch panel installed by overlapping the display device and receives an input of various types of information from presence of a touch on the screen display.

The output unit 7 is an interface for outputting various types of information to an external device and can output a detected pulse wave, can output a pulse obtained from a pulse wave or can output an alarm when a change appears in the pulse wave.

Moreover, the output unit 7 can make an output to another control device such as a controller for controlling a vehicle. The control device which received an output of a pulse wave or a heartbeat from the output unit 7 determines sleepiness or a tensed state of the driver (which will be described later), for example, and can perform control for the driver such as control of vibrating a steering wheel or a seat for awakening the sleepiness and an output of an alarm sound or a message, for example. Moreover, as control for the vehicle, at least any one of inter-vehicle distance control, vehicle speed control or brake control can be executed in accordance with the tensed state of the driver determined on the basis of the pulse wave. For example, if the control device determines that the driver is in a highly tensed state exceeding a predetermined value, it executes control such that the inter-vehicle distance is taken larger than a reference value, executes control such that a vehicle speed drops to a predetermined vehicle speed or less and executes deceleration processing by an automatic braking operation or the like if the vehicle speed is at the predetermined vehicle speed or more.

The camera 8 is constituted by using an optical system including a lens and an image sensor for converting an image formed by that to an electric signal and is installed so that the vicinity of the face of the user 10 comes to a photographing screen.

As the camera 8, an expensive one can be used, but a general-purpose product such as a web camera is used for the pulse wave detection device 1.

Since the pulse wave detection device 1 can detect the pulse wave favorably even with the camera 8 of a general-purpose product, a cost can be reduced.

The camera 8 takes a photo of a subject at a predetermined frame rate and outputs a moving image constituted by these continuous frame images (still images).

The frame image is constituted by an array of pixels which are minimum units constituting an image, and each pixel is color arranged by color components (R-value, G-value, B-value) of an RGB space.

The storage unit 9 is constituted by using a storage medium such as hard disk, an EEPROM (Electrically Erasable Programmable Read-Only Memory) and the like and stores programs and data for the CPU 2 to detect the pulse wave.

The storage unit 9 stores a pulse wave detection program 12, a user database 14, camera characteristic data 15 and the like.

The camera characteristic data 15 in them is data used in a third embodiment and will be described later.

The pulse wave detection program 12 is a program for causing the CPU 2 to execute the pulse wave detection processing.

The CPU 2 specifies the skin portion of the user in the moving image and detects a pulse wave from the specified skin portion by executing the pulse wave detection program.

The user database 14 is a database registering users using the pulse wave detection device 1.

The user database 14 stores registration data for each user such as a user 1, a user 2, . . . and the like.

Then, in the registration data, information specific to the user such as face data, skin color data, eye color data, . . . is registered.

The face data is feature of the face of the user made into data and is used for identifying the user seated in front of the camera 8 by face recognition.

The skin color data is data to be a reference of the color of the skin for specifying the skin portion of the user in the frame image. The skin portion is specified by comparison between the frame image and the skin color data.

The eye color data is data used in a second embodiment and will be described later.

FIG. 2 are a view for explaining the color space.

The pulse wave detection device 1 converts the color space of the frame image when detecting a pulse wave (it is called color conversion), and first, this will be explained.

A color image in general is expressed by three color components. In more detail, color information accompanying each pixel of an image is expressed as a coordinate value of a point in the color space extended using the three color components as axes.

In a general-purpose video camera, an R-component, a G-component, and a B-component of the RGB space are used as color components in many cases, and in the prior-art technologies, too, the R-, G-, and B-components included in the video signal are used as they are for pulse wave detection.

On the other hand, the inventor of the present application searched a more robust (resistant) color component against the disturbance elements.

As a result, it was found that the H component of an HSV space is suitable for specification of the skin portion, and the Q component in a YIQ space is suitable for pulse wave detection.

Thus, in the pulse wave detection device 1, the color component is used separately in accordance with the purpose.

As described above, since a reflection characteristic of the light is different depending on the observation targets, robustness against the disturbance can be further improved by selecting an optimal combination.

FIG. 2(a) is a view illustrating the RGB space.

The RGB space is constituted by an R-axis, a G-axis, and a B-axis representing RGB components and orthogonal to each other.

In the RGB space, color information is expressed by an R-value (red), a G-value (green), and a B-value (blue), and the RGB values of a pixel are specified by coordinate values of a point in the RGB space.

The RGB form is the most common color model, and the camera 8 also outputs a moving image in the RGB form.

Figure 2B:
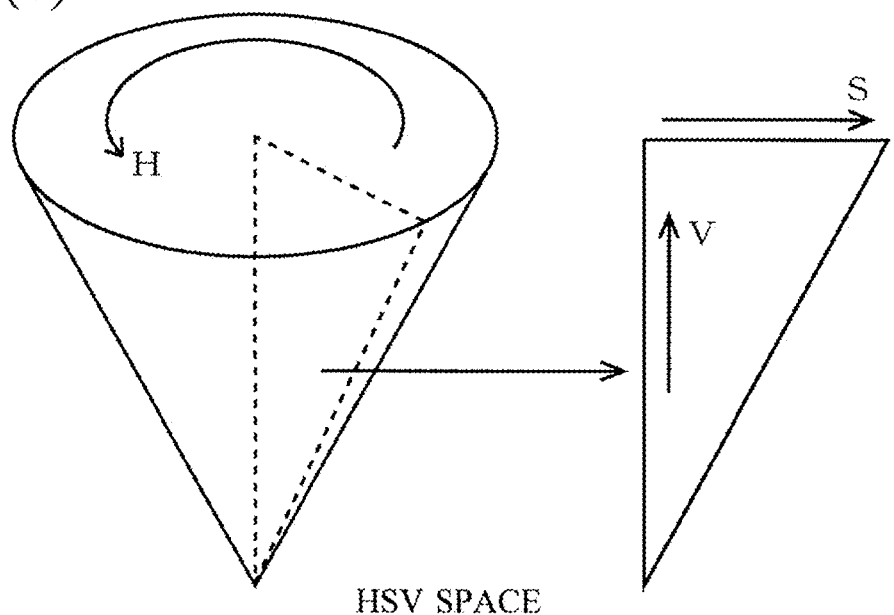

FIG. 2(b) is a view illustrating the HSV space.

The HSV space is expressed by a cone having a circular bottom surface, in which a rotation angle in a conical surface direction represents an H-component, a distance from a center in the bottom surface for an S-component, and a distance of a perpendicular line from a top of the cone to the bottom surface for a V-component.

In the HSV space, color information is expressed by an H-value (hue), an S-value (saturation), and a V-value (brightness), and an HSV value of a pixel are specified by coordinate values of a point in the HSV space.

The HSV form is used mainly in computer graphics.

The HSV space can be also expressed by a column in addition to the case expressed by a cone illustrated in FIG. 2(b). In this case, too, similar to the case expressed by a cone, a hue (H) changes along the outer periphery of the column, the saturation (S) changes with a distance from the center, and the brightness (V) changes from the top toward the bottom.

Figure 2C:
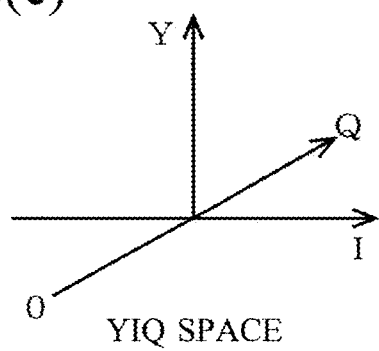

FIG. 2(c) is a view illustrating the YIQ space.

The YIQ space is constituted by a Y-axis, an I-axis, and a Q-axis representing YIQ components and orthogonal to each other.

In the YIQ space, color information is expressed by a Y-value (brightness), an I-value (chromaticity: warm color system), and a Q-value (chromaticity: cool color system), and a YIQ value of pixel is specified by a coordinate value of a point in the YIQ space.

The Y-value takes a positive value, and the I-value and the Q-value can take positive/negative values.

The YIQ form is used mainly in a video device as a form of a component signal generating an NTSC signal.

FIG. 3 are a view for explaining a mechanism for detecting a pulse wave from the moving image.

Figure 3A:
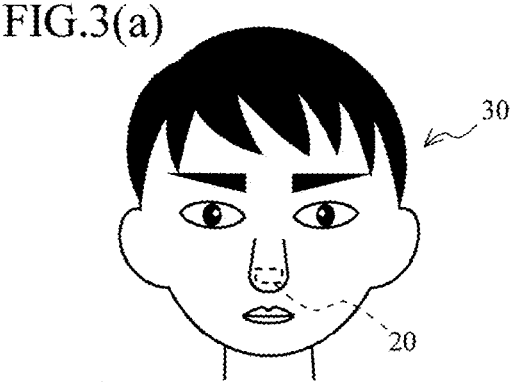
FIG. 3 are a view for explaining a mechanism for detecting a pulse wave from a moving image.

FIG. 3(a) is a view illustrating a method that the pulse wave detection device 1 samples skin color data from the face of the user.

The pulse wave detection device 1 takes a still image 30 of the face of the user by the camera 8, detects the nose and sets a nose region 20. Detection of the nose is made by using a general face recognition technology.

Then, the pulse wave detection device 1 converts the color space of the nose region 20 from the RGB space to the HSV space and generates skin color data from the H-value of each pixel.

The region where the skin color data is sampled is set to the nose region 20 because it can be specified easily by face recognition and a standard skin color is exposed.

Other than the nose, the skin color data can be sampled from the other regions such as a forehead and a cheek, for example.

Figure 3B:
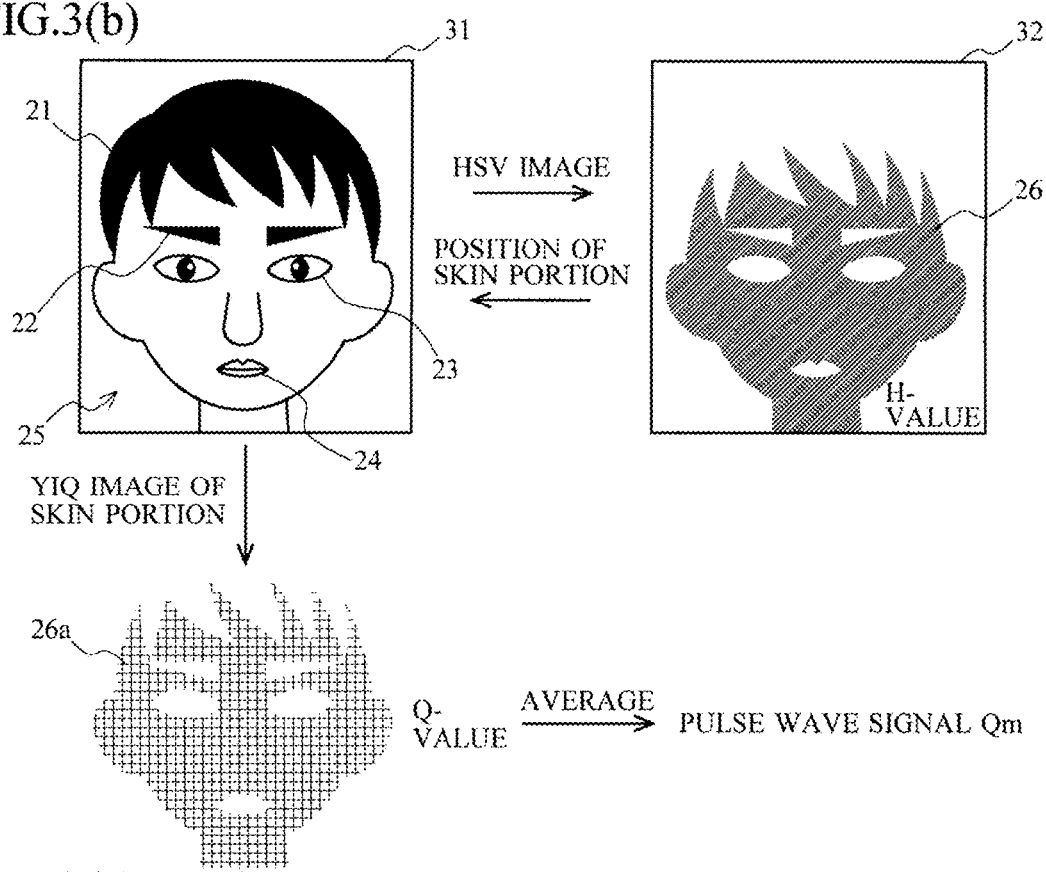

FIG. 3(b) is a view for explaining a method of extracting a pulse wave signal from the frame image 31.

In the frame image 31, hair 21, an eyebrow 22, an eye 23, a lip 24, a background 25 and the like are shown.

These portions other than the skin are portions which do not include a pulse wave signal or are not suitable for detection of the pulse wave signal and act as disturbance elements incurring accuracy drop in the pulse wave detection processing.

Thus, the pulse wave detection device 1 generates an HSV image 32 by color converting the frame image 31 and specifies a portion corresponding to the skin color data as a skin portion 26.

The skin portion 26 is specified by the pixel values and all the portions such as a neck where the skin is exposed are specified.

As described above, by ensuring the portion including the pulse wave signal to the maximum while excluding the disturbance elements, the pulse detection accuracy can be improved.

The pulse wave detection device 1 extracts the skin portion in the frame image 31 from a position of the skin portion 26 in the HSV image 32 and converts it to a YIQ image. As a result, a skin portion 26a in the YIQ space is obtained.

The pulse wave detection device 1 calculates Qm by averaging the Q-values of the pixels of the skin portion 26a and outputs Qm as a pulse wave signal.

It is to be noted that, in this embodiment, the frame image 31 is converted to the YIQ image and the skin portion 26a is obtained, but the skin portion 26a can be also obtained by converting the skin portion 26 in the HSV image 32.

Figure 3C:
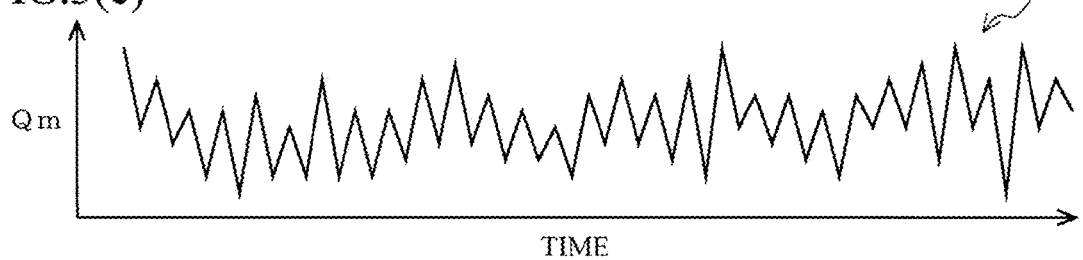

FIG. 3(c) is a view illustrating a pulse wave detected from the moving image.

The pulse wave detection device 1 arranges the pulse wave signal Qm output from each frame image in a time series (in the order of the frame images) and forms a pulse wave 35.

As described above, by specifying the skin portion of the user in each frame image, the pulse wave detection device 1 can detect a pulse wave while tracking/extracting the skin portion in accordance with movement of the user. As a result, the following features are obtained.

(Compatibility with Real-Time Processing)

In the prior-art technology, a moving image is taken while the subject is kept stationary in a state faced with the evaluation region 101. Since there is a possibility that the face goes out of the evaluation region 101 during photographing, the moving image after the photographing is analyzed.

On the other hand, since the pulse wave detection device 1 specifies the skin portion 26 in each frame image of the moving image, the evaluation region moves in the moving image as it is kept fixed to the skin of the user.

Since the skin portion does not go out of the evaluation region even if the face moves, the pulse wave can be detected on a real time basis.

Moreover, when the user's face is face recognized by each frame image and tracked, high computer processing capability is required, and a possibility of a failure of the face recognition is also high.

On the other hand, the pulse wave detection device 1 can track the skin portion with simple processing of specifying the skin portion by comparing the HSV image with the skin color data. Thus, it is suitable for the real-time processing.

Furthermore, since the pulse wave is detected by simple and low-load processing, drop of a frame (so-called drop frame) caused by the computer processing capability can be suppressed even in the real-time processing.

Since an interval between processed frame images is a measurement interval (sampling rate) of the pulse wave, widening of the measurement interval can be prevented by preventing the drop frame.

As a result, high time resolution of the pulse wave can be maintained, and detection accuracy of the pulse wave is improved.

Moreover, the face recognition processing is executed only at registration of the skin color data, and the skin color data already registered is used and thus, such a situation that the face recognition fails at a site and the skin color data cannot be sampled, which makes pulse detection impossible can be avoided, whereby measurement reliability is improved.

The pulse wave detection is mainly used in a case of monitoring a current physiological state of a target, and capability of real-time processing is important.

(Exclusion of Background)

In the prior-art technology, since it is difficult to match the evaluation region 101 with the shape of the subject's face, the disturbance element such as a background is included in the evaluation region 101, which might lower detection accuracy of the pulse wave.

On the other hand, in the pulse wave detection device 1, the evaluation region and the skin portion 26 match each other at all times and thus, inclusion of the disturbance element such as the background other than the face in the evaluation region can be prevented, whereby accurate pulse wave detection can be made.

(Exclusion of Face Portion not Relating to Pulse Wave)

In the prior-art technology, even when the subject's face is correctly set to the evaluation region 101, the face portions not relating to the pulse wave (hair, eye, mouth and the like) are included in the evaluation region and thus, it is likely that they affect the detection accuracy of pulse wave as the disturbance elements.

On the other hand, in the pulse wave detection device 1, since these face elements are excluded from the skin portion 26, the detection accuracy of the pulse wave can be improved.

Furthermore, even if the user blinks or opens/closes the mouth, since the skin portion 26 is dynamically set in accordance with the movement of the face, the disturbance elements by the face movement can be also excluded from the evaluation region.

FIG. 4 is a flowchart for explaining a procedure of entire processing executed by the pulse wave detection device 1.

The following processing is executed by the CPU 2 in accordance with the pulse wave detection program 12.

First, when the CPU 2 detects that the user is seated at a designated position from a change in the image of the camera 8, it obtains an image of the user's face and stores it in the RAM 4 (Step 5).

This image may be taken as a still image or may be taken out of a frame image of the moving image.

As described above, the pulse wave detection device 1 includes moving image obtaining means for obtaining a moving image taking a region including at least the skin of the target, and the region including the skin includes the face of the target.

Subsequently, the CPU 2 face recognizes the image of the face stored in the RAM 4 and searches this by collating it with the face data in the user database 14 (Step 10).

When the face is searched, the CPU 2 determines that the user has been registered (Step 15; Y) and obtains the skin color data of the user from the user database 14 and stores it in the RAM 4 (Step 20).

On the other hand, when the face has not been searched, the CPU 2 determines that the user has not been registered yet (Step 15; N), executes the skin color data sampling processing and samples the skin color data from the image of the face (Step 25).

Then, the pulse wave detection device 1 generates face data from the image of the face and makes user registration by associating the face image with the skin color data and storing it in the user database 14 (Step 27).

When the CPU 2 obtains the skin color data, it obtains a frame image from the moving image transmitted from the camera 8 and stores it in the RAM 4 (Step 30).

Subsequently, the CPU 2 executes the pulse wave detection processing for processing a pulse wave from the frame image stored in the RAM 4 (Step 35).

Subsequently, the CPU 2 determines whether the pulse wave detection is to be continued or not (Step 40).

When the pulse wave detection is to be continued (Step 40; Y), the pulse wave detection device 1 returns to Step 30 and executes the pulse wave detection processing to the subsequent frame image in the moving image.

On the other hand, if the pulse wave detection is not to be continued since the user presses a stop button or the like (Step 40; N), the pulse wave detection device 1 finishes the processing.

Figure 5:
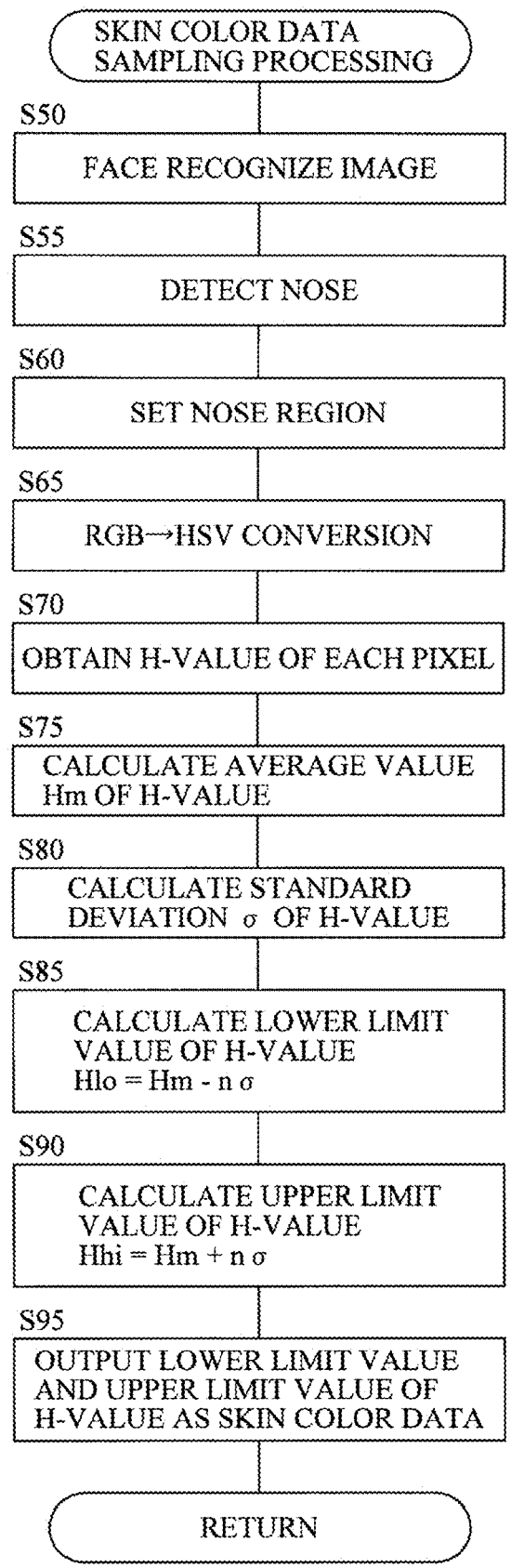
FIG. 5 is a flowchart for explaining a procedure of skin color data sampling processing.

FIG. 5 is a flowchart for explaining a procedure of the skin color data sampling processing at Step 25.

First, the CPU 2 reads out an image of the face from the RAM 4 and face recognizes it (Step 50) and then, detects the nose (Step 55).

Subsequently, the CPU 2 sets a nose region for sampling the skin color data sampling to the detected nose (Step 60).

As described above, the pulse wave detection device 1 includes face image obtaining means for obtaining an image taking the face of the target and region specifying means for specifying a predetermined region (nose region) where the face skin is exposed.

Subsequently, the CPU 2 color converts the color space of the nose region from the RGB space to the HSV space (Step 65) and obtains the H-value of each pixel (Step 70).

Subsequently, the CPU 2 calculates Hm by averaging the H-value of each pixel (Step 75) and moreover, calculates a standard deviation $\sigma$ of the H-value (Step 80).

Subsequently, the CPU 2 calculates a lower limit value $Hlo=Hm-n\times\sigma$ of the H-value from Hm and $\sigma$ and stores it in the RAM 4 (Step 85). Reference character n will be described later.

Furthermore, the CPU 2 calculates an upper limit value $Hli=Hm+n\times\sigma$ of the H-value from Hm and $\sigma$ and stores it in the RAM 4 (Step 90).

Then, the CPU 2 outputs the lower limit value and the upper limit value of the H-value as the skin color data (Step 95) and returns to a main routine (FIG. 5).

The output skin color data (Hlo and Hhi) functions as a reference component which is a color space component to be a reference for specifying the skin portion of the target and is registered in the user registration at Step 27 (FIG. 4).

As described above, the pulse wave detection device 1 includes reference component registering means for registering a reference component and applies statistical processing by an average value and a standard deviation to the color space component of the nose region and makes registration.

Reference character n is a multiplier of $\sigma$ and specifies a range of the H-value around Hm. As will be described later, the pulse wave detection device 1 specifies a portion where the H-value is within this range from the frame image as the skin portion and thus, reference character n can be adjusted to an appropriate value through experiments or the like.

By setting n=3, for example, a portion where the H-value is within a range of $Hm\pm3\sigma$ is specified as the skin portion.

FIG. 6 is a flowchart for explaining a procedure of the pulse wave detection processing at Step 35 (FIG. 5).

First, the CPU 2 coverts the color space of the frame image stored in the RAM 4 from the RGB space to the HSV space and stores the converted HSV image in the RAM 4 (Step 100).

Subsequently, the CPU 2 sets a counter i counting the order the pixel to i=0 (Step 103).

Subsequently, the CPU 2 obtains Hi which is the H-value of the i-th pixel in each pixel of the HSV image stored in the RAM 4 (Step 105).

Then, the CPU 2 determines whether Hi satisfies Hlo<Hi<Hhi or not, that is, whether Hi is within a range of the skin color data (Step 110).

When Hi is within this range, the CPU 2 determines that the pixel corresponds to the skin color data.

When Hi satisfies the inequality, that is, when Hi corresponds to the skin color data (Step 110; Y), the CPU 2 stores a position coordinate of the pixel in the RAM 4 (Step 115).

After the position coordinate is stored at Step 115 or when Hi is not within the range of the skin color data at Step 110 (Step 110: N), the CPU 2 determines whether the determination at Step 110 has been made for all the pixels in the HSV image or not (Step 120).

If there still is a pixel which has not determined yet (Step 120; N), the CPU 2 increments I by 1 and updates it to i=i+1 (Step 123), returns to Step 105 and repeats the similar processing to the subsequent pixel.

By executing Step 100 to Step 123 described above, the position coordinate of corresponding to the skin portion is stored in the RAM 4.

Subsequently, the CPU 2 obtains the pixel to be evaluated in the frame image by specifying the pixel located at the position coordinate stored in the RAM 4 in the frame image (Step 125).

As described above, the pulse wave detection device 1 includes skin portion specifying means for specifying a skin portion of the target (pixel to be evaluated) shown on the moving image.

Moreover, this specification is made by taking the portion where the predetermined color space component in the moving image corresponds to the reference component as the skin portion by the pixel values.

Subsequently, the CPU 2 color converts the color space of the pixel to be evaluated from the RGB space to the YIQ space (Step 130).

Then, the CPU 2 calculates the average value Qm by averaging the Q-values of the pixels (Step 135), outputs it as the pulse wave signal (Step 140), and returns to the main routine (FIG. 4).

The pulse wave signal is superimposed on the Q-value of the pixel to be evaluated, and by averaging it to Qm, an influence of noise can be reduced.

By means of the processing described above, the pulse wave signal Qm is detected in one frame image, and by executing this to each of the continuing frame images and by arranging the pulse wave signals Qm in the order the frame images, a pulse wave illustrated in FIG. 3(c) is obtained by a temporal change of the pulse wave signal Qm.

As described above, the pulse wave detection device 1 includes pulse wave obtaining means for obtaining a pulse wave from the temporal change of the predetermined color space component in the skin portion and output means for outputting it.

As described above, the pulse wave detection device 1 carries out specification of the skin portion with the H component in the HSV space and the pulse wave detection with the Q component in the YIQ space.

Thus, the color space component used by skin portion specifying means for specifying the skin portion and the color space component used by the pulse wave obtaining means for obtaining the pulse wave are color space components different from each other.

Then, the pulse wave detection device 1 includes color space converting means for converting the color space of the moving image, and the skin portion specifying means and the pulse wave obtaining means obtain the color space component in the color space converted by the color space converting means.

Furthermore, the pulse wave detection device 1 can include monitoring means for monitoring a physical condition of the passenger of the transportation equipment by the pulse wave.

It is to be noted that, in this embodiment, after the skin portion is extracted from the frame image, the extracted skin portion is color converted from the RGB space to the YIQ space, but it may be so configured that the entire frame image is color converted to the YIQ space and then, the skin portion is extracted.

Second Embodiment

In the prior-art technology, pulse wave detection is made under the stable brightness by sunlight incident through the window of the laboratory.

On the other hand, when the pulse wave detection device 1 is to be used in a vehicle or at a medical site, photographing environments in use are varied, and particularly the brightness is expected to be changed during the pulse wave detection. Particularly when the pulse wave of a driver or a passenger is to be detected in the vehicle, a change in the brightness can frequently occur depending on a change in a running position or direction of the vehicle and a time slot.

Thus, whether or not a detection result is influenced by a brightness change caused when the pulse wave detection device 1 is actually used was examined. That is, the inventor of the present application changed the brightness by casting a shadow on the face of the subject using a round fan while the pulse wave was being detected under illumination by a fluorescent lamp.

FIG. 7 are a view illustrating a result by the experiment.

Figure 7A:
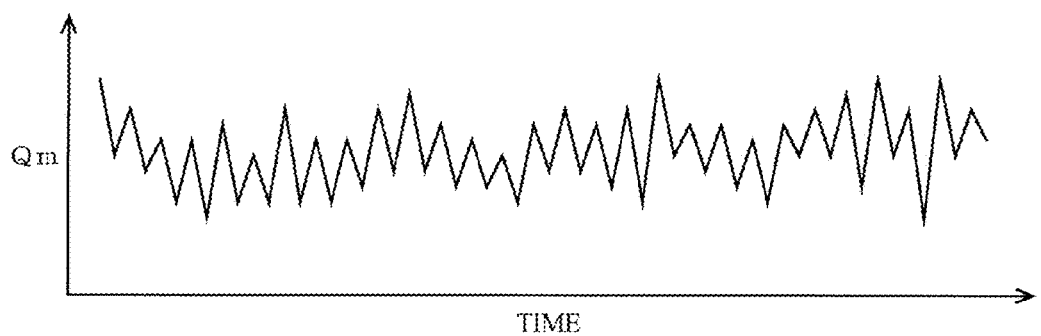
FIG. 7 are a view illustrating a result by an experiment.

FIG. 7(a) shows a temporal change of the pulse wave signal Qm when the brightness of the environment is not changed.

As illustrated in the figure, the pulse wave is clearly detected.

Figure 7B:
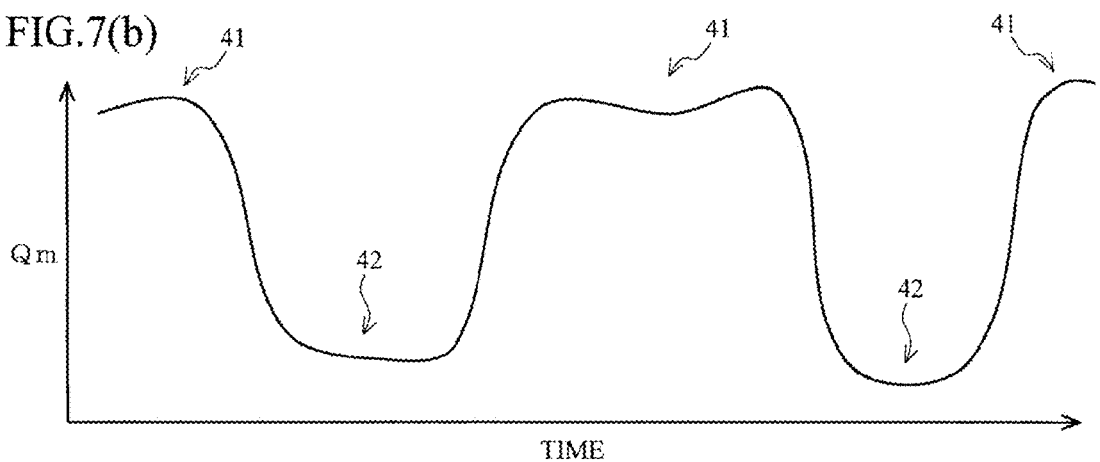

On the other hand, FIG. 7(b) shows a temporal change of the pulse wave signal Qm when only the brightness is changed by casting a shadow on the face of the subject by using a round fan.

A period 41 is a period without a shadow, while a period 42 is a period with a shadow.

As illustrated in the figure, the pulse wave signal Qm is largely changed by a change in the brightness, and a change in Qm is hidden in this change, which makes detection of the pulse wave difficult.

The inventor of the present application made a study on this problem and found that the pulse wave signal Qm does not appear in a portion of the eye (hereinafter, referred to as an eye portion).

Since the pulse wave signal Qm on which the brightness change is superimposed is detected from the skin portion and the brightness change (or intensity of the brightness) not including the pulse wave is detected from the eye portion, the brightness change can be corrected by subtracting the latter from the former.

Moreover, the inventor of the present application found that the Y component of the YIQ space is suitable for detection of the brightness change and in this embodiment, the brightness change is detected with the Y component.

Moreover, since the pulse wave signal Qm and the Y-value of the brightness belong to the same color space, it is only necessary to carry out subtraction.

Each figure in FIG. 8 is a view for explaining a correcting method of the brightness change.

FIG. 8(a) is a view illustrating the eye portion 45 used for detection of the brightness change.

The eye portion 45 is constituted by a pupil portion 48 which is dark in color and located substantially at the center, an iris portion 47 around the pupil portion 48, and a white eye portion 46 which is close to white and located on an outer side of the iris portion 47.

The pulse wave detection device 1 sets a minimum value of the Q-value in the eye portion 45 to Qlo and a maximum value of the Q-value in the eye portion 45 to Qhi and registers them as eye color data.

It is to be noted that the pulse wave detection device 1 may set the Q-value of the white eye portion 46 to Qlo and the Q-value of the pupil portion 48 to Qhi and register them as the eye color data.

As will be described later, the pulse wave detection device 1 extracts the eye portion 45 from the eye region in the face of the user by using the eye color data and detects a change in brightness from a change in the Y-value of the extracted eye portion 45.

FIG. 8(b) is a view illustrating a brightness signal 51. The pulse wave detection device 1 averages the Y-value signal and generates Ym. By plotting this in a time series, the brightness signal 51 is obtained.

In the illustrated example, since the shadow was made on the face in the period 42, the brightness in the period 42 is smaller than that in the period 41.

FIG. 8(*c*) is a view illustrating a before correction pulse wave signal 52.

The after correction pulse wave signal 52 is obtained by plotting the pulse wave signals Qm in a time series before the change in the brightness is corrected.

The pulse wave signal 52 before correction is subjected to an influence of the drop in brightness as illustrated in FIG. 8(*c*), and the pulse wave signal Qm in the period 42 also drops.

FIG. 8(*d*) is a view illustrating an after correction pulse wave signal 53.

The pulse wave detection device 1 generates the after correction pulse wave signal 53 by subtracting the brightness signal Ym from the pulse wave signal Qm before the correction. By plotting it in a time series, the after correction pulse wave signal 53 is obtained.

In the after correction pulse wave signal 53, since the influence by the change in the brightness has been removed, an appropriate pulse wave can be obtained even in the period 42 when the brightness drops.

FIGS. 8(*e*) and 8(*f*) are views for explaining a method of specifying the eye portion 45 in the frame image in the moving image by the pulse wave detection device 1.

First, the pulse wave detection device 1 applies the face recognition processing to the frame image as illustrated in FIG. 8(*e*) and extracts the eye region 55 including the eye portion 45.

Then, the pulsed wave detection device 1 applies the eye color data to the eye region 55 and extracts the eye portion 45.

The eye portion 45 is extracted from the eye portion 55 as above because of the following reason.

If the eye color data is applied to the frame image, a portion accidentally corresponding to the eye color data such as a background can be extracted, for example, but since the eye region 55 is constituted by the skin portion and the eye portion 45, and the portion corresponding to the eye color data is only the eye portion 45 and thus, the eye portion 45 can be reliably specified.

Moreover, it is possible to directly specify the eye portion 45 by the face recognition, but accuracy of the face recognition needs to be improved, and a failure rate is also raised and thus, the eye region 55 is roughly specified in the image recognition as described above.

FIG. 9 is a flowchart for explaining a procedure of entire processing executed by the pulse wave detection device 1.

The same Steps as those in the first embodiment are given the same Step numbers, and the explanation will be simplified or omitted.

If the user is a registered user (Step 15; Y), the CPU 2 obtains the skin color data from the user database 14 (Step 20) and further obtains the eye color data (Step 150).

On the other hand, if the user is not a registered user (Step 15; N), the CPU 2 executes the skin color data sampling processing (Step 25) and further executes the eye color data sampling processing (Step 155) and registers the user by storing face data, skin color data, eye color data and the like in the user database 14 (Step 27).

The CPU 2 obtains the frame image (Step 30), executes the pulse wave detection processing (Step 35), and detects the pulse wave signal Qm before correction.

Subsequently, the CPU 2 executes the brightness change measure processing to the pulse wave signal Qm before correction (Step 160) and outputs the pulse wave signal Qm after correction.

Figure 10:
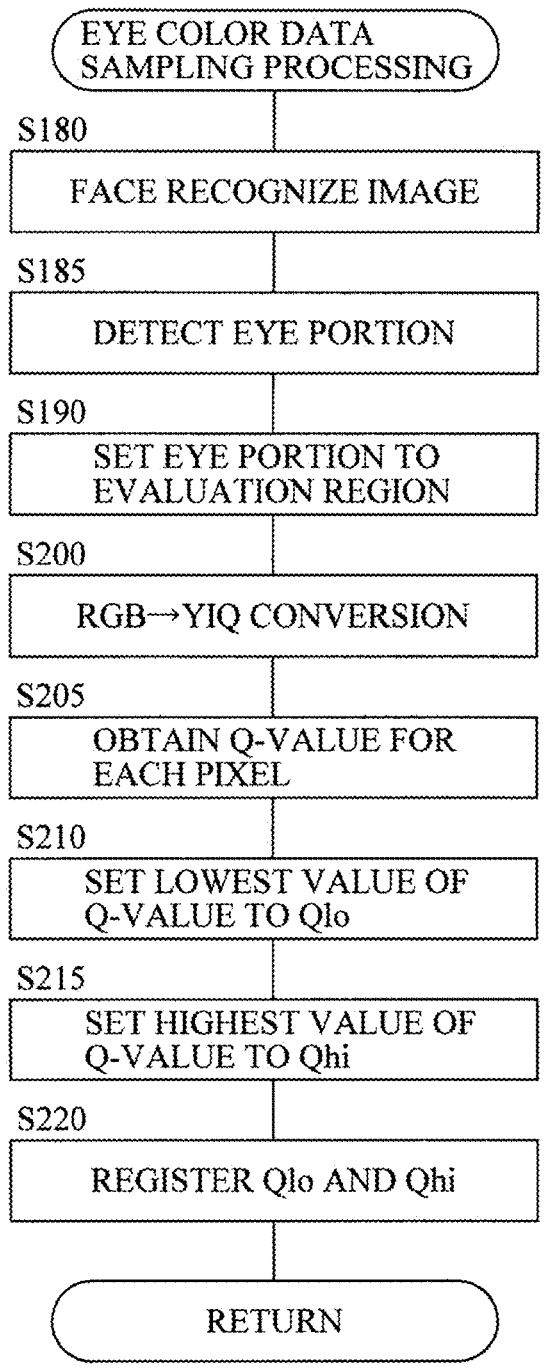
FIG. 10 is a flowchart for explaining a procedure of eye color data sampling processing.

FIG. 10 is a flowchart for explaining a procedure of the eye color data sampling processing at Step 155.

First, the CPU 2 face recognizes the image of the face used in the skin color data sampling processing (Step 180) and detects the eye portion (Step 185).

The pulse wave detection device 1 includes region specifying means for specifying the eye region in the face (the eye portion in this case) by the face recognition processing in the face image.

Subsequently, the CPU 2 specifies the eye portion to an evaluation region (Step 190) and converts the color spaces of all the pixels included in the eye portion from the RGB space to the YIQ space (Step 200).

Subsequently, the CPU 2 obtains the Q-value for each pixel included in the eye portion and stores it in the RAM 4 (Step 205).

Then, the CPU 2 sets a lowest value of the Q-value stored in the RAM 4 to Qlo (Step 210) and moreover, a highest value to Qhi (Step 215), makes them the eye color data and registers it in association with the face data and the skin color data of the user in the user database 14 (Step 220) and returns to the main routine (FIG. 9).

As described above, the pulse wave detection device 1 includes reference-component registering means for registering the color space components of the specified region as reference components (Qlo and Qhi) which become references for specifying the eye portion.

Then, the reference-component registering means registers a value to which statistical processing for specifying the minimum value and the maximum value to distribution of the color space components in the specified region.

Figure 11:
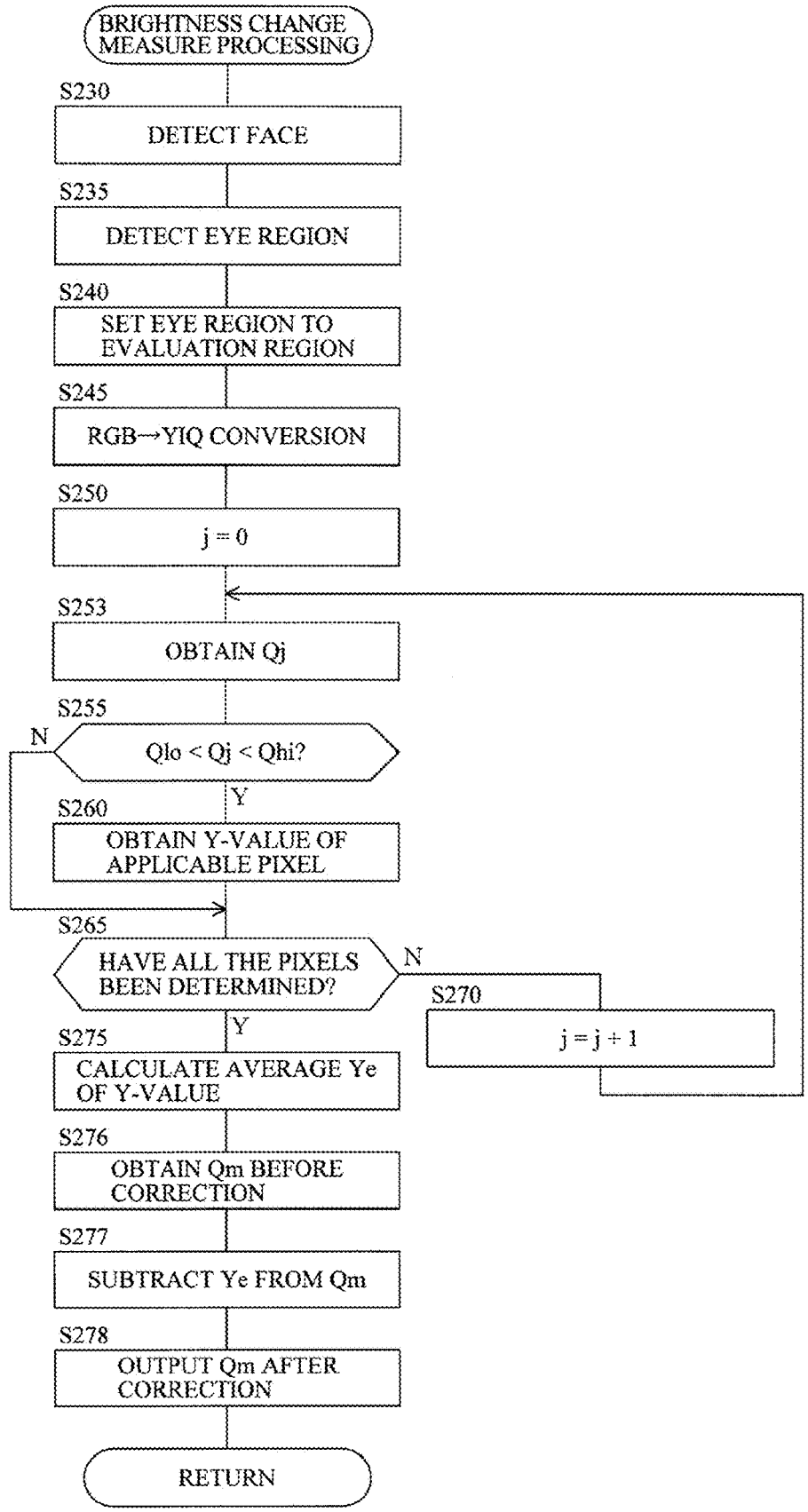
FIG. 11 is a flowchart explaining a procedure of brightness change measure processing.

FIG. 11 is a flowchart for explaining a procedure of the brightness change measure processing at Step 160.

First, the CPU 2 of the pulse wave detection device 1 detects the face by executing the face recognition in the frame image stored in the RAM 4 (Step 230) and moreover, detects the eye region (Step 235) and sets the detected eye region to the evaluation region (Step 240).

Subsequently, the CPU 2 converts the color space of the eye region from the RGB space to the YIQ space and stores it in the RAM 4 (Step 245).

Subsequently, the CPU 2 sets a counter j to 0 (Step 250) and obtains Qj which is the Q-value of a j-th pixel in the eye region from the RAM 4 (Step 253).

Then, the CPU 2 determines a size relationship among Qj, Qlo, and Qhi (Step 255).

In a case of Qlo<Qj<Qhi (Step 255; Y), the CPU 2 determines that the pixel is included in the eye portion and obtains the Y-value of the pixel and stores it in the RAM 4 (Step 260).

After the Y-value is obtained or if Qlo<Qj<Qhi is not satisfied (Step 255; N), the CPU 2 determines whether or not the determination has been made for all the pixels (Step 265).

If there still is a pixel which has not been determined yet (Step 265; N), the CPU 2 increments j by one and updates it to j=j+1 (Step 270) and then, returns to Step 253 and repeats the similar processing to the subsequent pixel.

By means of the processing described above, the Y-value of each pixel of the eye portion obtained by excluding the skin portion from the eye region is obtained.

As described above, the pulse wave detection device 1 includes eye portion specifying means for specifying the eye portion shown on the moving image by the pixel values by specifying a portion where the predetermined color space component corresponds to the registered reference component in the moving image as the eye portion.

After storing the Y-values of all the pixels as above in the RAM 4, the CPU 2 calculates an average value Ye by averaging them (Step 275).

The average value Ye corresponds to the brightness of a photographing environment and a difference from Ye in the frame images before and after that indicates a change in brightness.

Thus, by subtracting the average Ye of the respective brightness from each of the frame images, a change portion in the brightness can be corrected.

As described above, the pulse wave detection device 1 includes brightness change obtaining means for obtaining a change in brightness caused by a change in the photographing environment of the moving image from a change in the predetermined color space component of the eye portion.

Subsequently, the CPU 2 obtains the pulse wave signal Qm before correction (Step 276), obtains the pulse wave signal Qm after correction by subtracting the average value Ye from that (Step 277), outputs the calculated pulse wave signal Qm after correction (Step 278) and returns to the main routine (FIG. 9).

As described above, the pulse wave detection device 1 includes brightness correcting means for correcting brightness of the moving image by using a change in the brightness by the pixel values and pulse wave obtaining means for obtaining a pulse wave from a temporal change of the predetermined color space component in the corrected skin portion.

Moreover, the pulse wave detection device 1 obtains a change in the brightness with the Y component, specifies the skin portion with the H component and detects the pulse wave with the Q component and executes processing with different color components.

Then, the pulse wave detection device 1 includes color space converting means for converting these color spaces.

By means of the second embodiment described above, the following effects can be obtained.

(1) The pulse wave can be detected even when the brightness is changed by a change in the photographing environment such as change in light from outside, movement of the user or the like;

(2) The change in the brightness can be detected from the eye at the same time as the pulse wave is detected from the skin of the face; and (3) The change in brightness can be corrected even without a special device.

It is to be noted that, in this embodiment, the brightness of the skin portion is corrected after the skin portion is extracted from the frame image but the skin portion may be extracted after the brightness correction is applied to the entire frame image.

Third Embodiment

When the general-purpose camera 8 is used, for example, it is not known in a case where a human being appreciates a moving image, but there is fluctuation in characteristics in each pixel to such a degree that obstructs detection of the pulse wave.

In this embodiment, since the pulse wave is detected by the color component, it is affected by the fluctuation in chrominance (color quality) characteristics.

FIG. 12 are a view for explaining the fluctuation in chrominance by the camera characteristics.

Figure 12A:
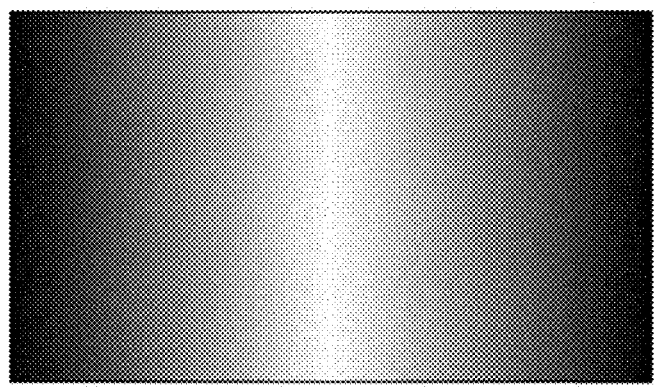
FIG. 12 are a view for variation in chrominance.

FIG. 12(a) is a view illustrating the fluctuation in the chrominance characteristics of the pixel in the camera 8 by contrast.

Since the chrominance characteristics are not uniform as above, if the user moves in the screen, a value of the chrominance is changed, which affects accuracy of pulse wave detection.

Figure 12B:
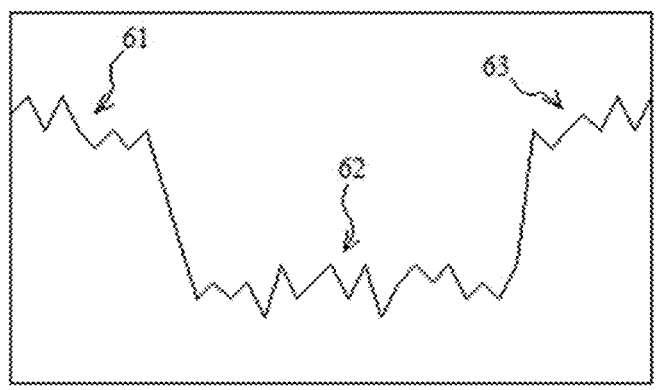

FIG. 12(b) is a view illustrating comparison of the detected pulse waves in a left region 61, a center region 62, and a right region 63 in the screen by having the subject move in the screen.

As illustrated in the figure, though the pulse waves at the same time should have been detected, a difference is caused in a height of the level by the difference in the chrominance.

Conventionally, the chrominance characteristics of the camera are corrected by an expert using a chart for calibration for various colors. This requires specialized knowledge and takes many processes, which is difficult for general uses.

Moreover, since correction is made for various colors, correction processing is complicated, and when the pulse wave is processed on the real time basis, drop of a frame occurs and it is likely that a rate relating to processing lowers.

Thus, in this embodiment, the color to be corrected is limited to the color of the user's face, and an average value of the chrominance for each pixel generated by movement of the user in the screen is stored as camera characteristic data.

By correcting a change in the chrominance by using the camera characteristic data, more accurate pulse wave can be detected.

Moreover, the movement of the user in the screen causes the skin portion to sweep the screen, but the pulse wave detection device 1 consecutively corrects the pixel in the region swept by the skin portion.

As described above in this embodiment, a correction value can be created automatically with movement of the user in the screen.

Figure 13:
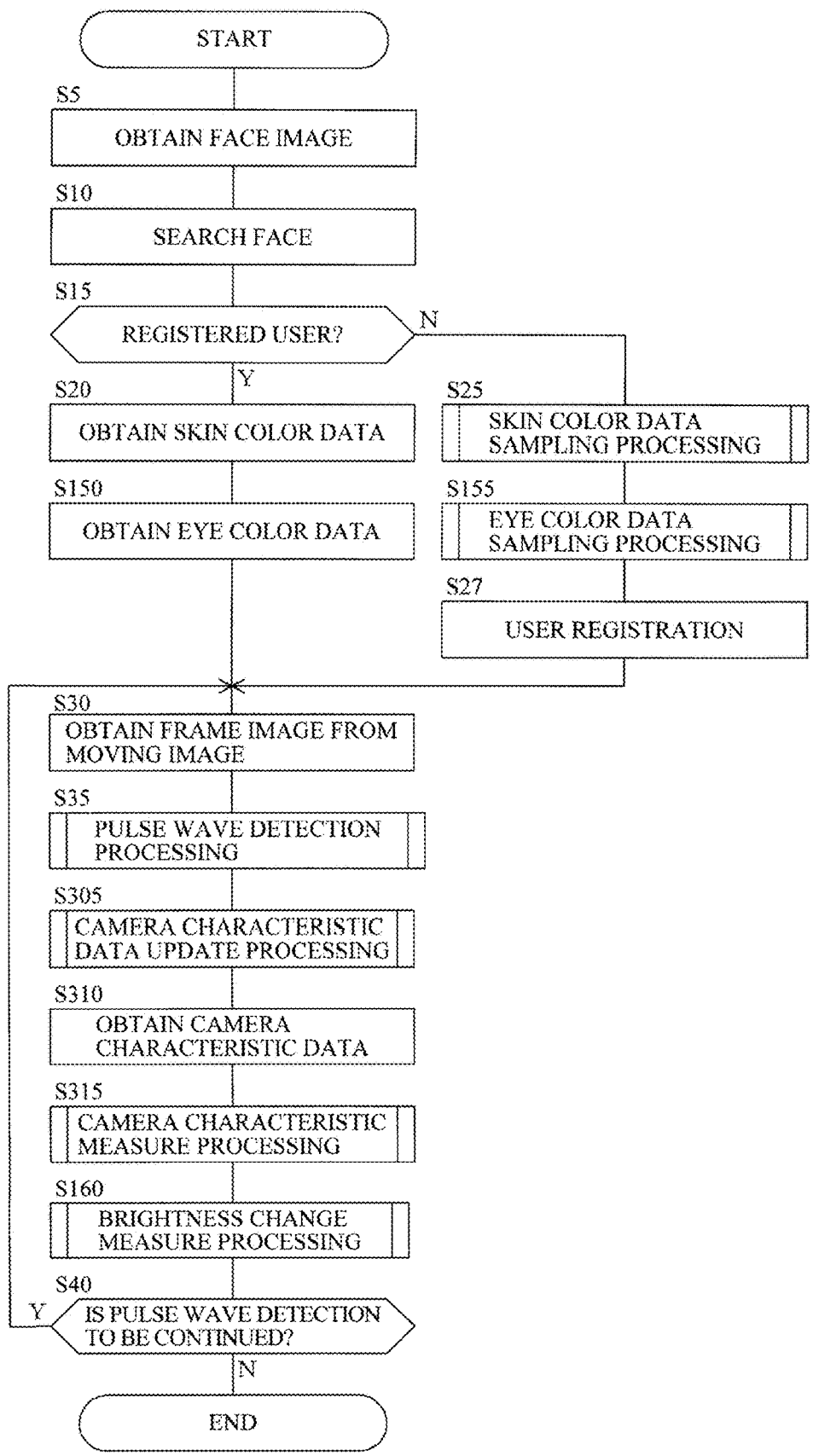
FIG. 13 is a flowchart for explaining a procedure of entire processing in a third embodiment.

FIG. 13 is a flowchart for explaining a procedure of entire processing executed by the pulse wave detection device 1.

The same Steps as those in the first embodiment and in the second embodiment are given the same Step numbers, and the explanation will be simplified or omitted.

After Step 5 to Step 30, the CPU 2 executes the pulse wave detection processing (Step 35) and then, executes camera characteristic update processing (Step 305).

Then, the CPU 2 obtains the updated latest camera characteristic data (Step 310) and applies correction by camera characteristic measure processing to the pulse wave signal Qm by using it (Step 315).

After that, the CPU 2 executes the brightness change measure processing to the pulse wave signal Qm to which the correction is applied by the camera characteristic (Step 160).

Figure 14:
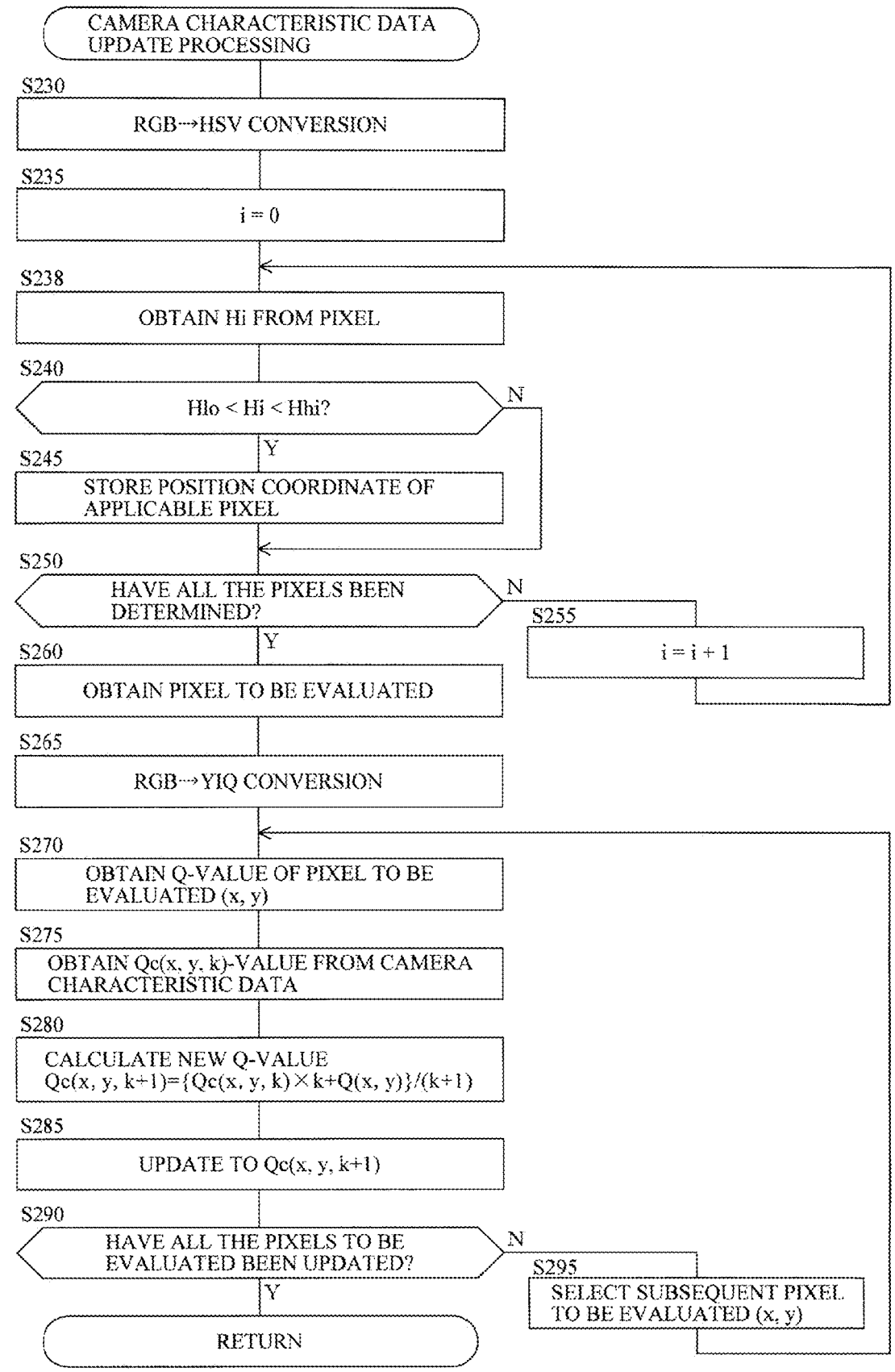
FIG. 14 is a flowchart for explaining a procedure of camera-characteristic data update processing.

FIG. 14 is a flowchart for explaining a procedure of the camera characteristic data update processing at Step 305 (FIG. 14).

Steps 230 to 265 are the same as Steps 100 to 130 in FIG. 6.

That is, the CPU 2 designates the pixel applicable to the skin portion in the frame image as a pixel to be evaluated and converts its color space from the RGB space to the YIQ space (Step 265).

Subsequently, the CPU 2 selects a pixel at a position coordinate (x, y) in the pixels to be evaluated (a selecting method may be an arbitrary algorithm), obtains the Q-value and stores it in the RAM 4 (Step 270).

Subsequently, the CPU 2 obtains the latest correction value (that is, the latest value until the previous correction) Qc(x, y, k) applicable to the position coordinate from the camera characteristic data 15 and stores it in the RAM 4 (Step 275).

Here, reference character k is a counter set for each pixel and is a parameter indicating a number of correction times of the pixel until the previous time.

Subsequently, the CPU 2 calculates a new Qc-value by the following equation by using these values stored in the RAM 4 and stores its result in the RAM 4 (Step 280).

$$Qc(x,y,k+1)=\{Qc(x,y,k)\times k+Q(x,y)\}/(k+1)$$

Subsequently, the CPU 2 updates Qc (x, y, k) of the camera characteristic data 15 with Qc(x, y, k+1) (Step 285).

As described above, the pulse wave detection device 1 includes update means for updating the correction value for each pixel by applying predetermined statistical processing to a change in the color space component generated on the skin portion with movement of the face in order to update the correction value for each pixel by using the statistical processing by the equation above.

Subsequently, the CPU 2 determines whether the Qc values have been updated for all the pixels to be evaluated or not (Step 290).

If there still is a pixel which has not been updated yet (Step 290; N), the CPU 2 selects the subsequent pixel to be evaluated (x, y) (Step 295) and then, returns to Step 270, and when update has been made for all the pixels (Step 290; Y), the CPU 2 finishes the update processing and returns to the main routine (FIG. 13).

Figure 15:
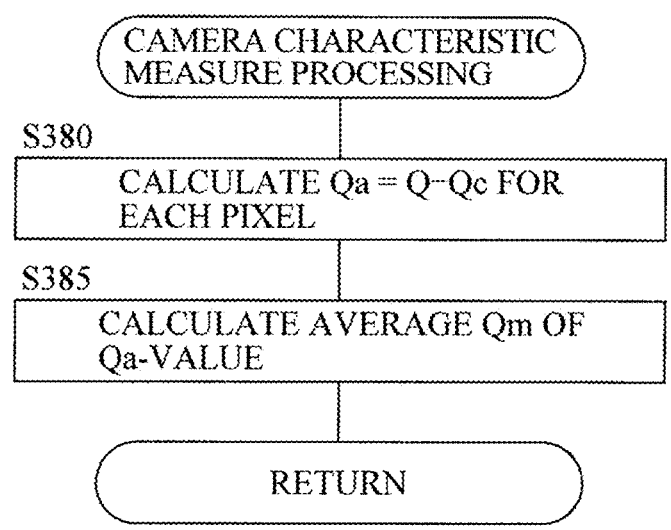
FIG. 15 is a flowchart for explaining a procedure of camera-characteristic measure processing.
Figure 16A:
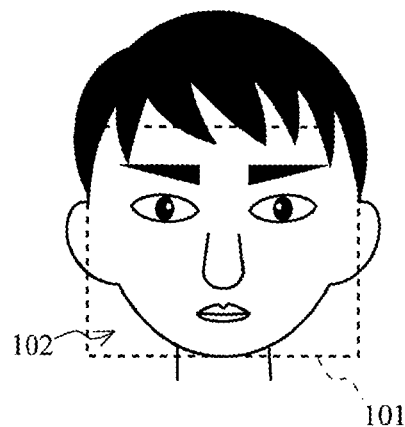
FIG. 16 are a view for explaining a prior-art technology.
Figure 16B:
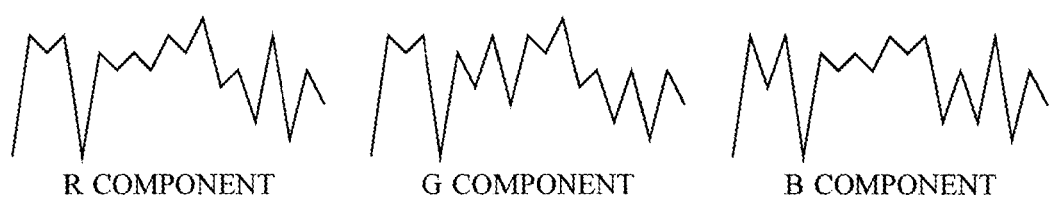

FIG. 15 is a flowchart for explaining a procedure of the camera characteristic measure processing at Step 315 (FIG. 13).

The CPU 2 calculates Qa (Q-value corrected by the camera characteristic measure) by subtracting Qc from the Q-value for each pixel set as the pixel to be evaluated in the frame image (Step 380), calculates an average value of Qa and sets it to the pulse wave signal Qm (Step 385) and returns to the main routine.

As described above, the pulse wave detection device 1 includes fluctuation correcting means for correcting fluctuation in the predetermined color space component generated in the moving image caused by the camera characteristics by using a correction value corresponding to the pixel for each pixel, pulse wave obtaining means for obtaining a pulse wave from a temporal change of the color space component in the corrected skin portion, and output means for outputting the pulse wave.

Furthermore, the pulse wave detection device 1 corrects the fluctuation by using the latest correction value while the correction value is updated and obtains the pulse wave from the skin portion corrected by the latest correction value by executing the camera characteristic data update processing at Step 305 (FIG. 13) and the camera characteristic measure processing at Step 315 (FIG. 13) in the same loop processing.

As described above, the pulse wave detection device 1 outputs the pulse wave signal Qm by using the latest correction value while correcting the camera characteristics.

Moreover, the camera characteristic measure processing can be configured to finish the correction when the correction value is converged to a certain degree.

In that case, correction is continued at least until the fluctuation by the camera characteristics becomes smaller than the fluctuation by the pulse wave signal.

As described above, the camera characteristic data 15 is completed and by subsequently using this characteristic, it is no longer necessary to execute the camera characteristic update processing in the pulse wave detection. As a result, a load of the CPU 2 is reduced, and that portion can be allocated to the other processing.

In this case, the pulse wave detection device 1 completes update of the correction value when the size of fluctuation in the color space components caused by the camera characteristics is converged to a value smaller than the size of the change in the color space components by the pulse wave.

According to the third embodiment, the following effects can be obtained.

(1) The camera characteristics can be detected and corrected while the pulse wave detection device 1 is in use. Thus, prior adjustment is not needed.

(2) Since the correction value is made with the movement of the user, it is suitable to be mounted on a vehicle and used for a passenger as a target, for example.

(3) Since the color to be corrected is limited to the color of the face, complicated calibration calculation is not needed, and drop of frame during moving image processing can be suppressed.

(4) As the result of suppression on the drop of a frame, time resolution of the pulse wave is improved. Thus, this is suitable for the real-time processing, and accuracy of pulse interval is also improved.

Subsequently, timing to start the processing by the pulse wave detection device 1 (FIGS. 4, 9, and 13) in the aforementioned first to third embodiments will be explained.

In each of the embodiments, the pulse wave detection processing by the pulse wave detection device 1 is started at any one of the following timings. As each of the start timings, timing 1 may be set to default so that the user can change at arbitrary timing.

(1) Timing 1

The processing is started when the fact that the driver who is a monitoring target of the pulse wave is seated on a driver's seat is detected.

It is to be noted that, when a passenger other than the driver (a passenger on a seat next to the driver's seat or on a rear seat) is also a monitoring target of the pulse wave, the processing is started when the passenger is seated on any one of the seats to be targets.

In this case, regarding detection of the passenger, any one of cases where a load sensor is disposed on a seat to be a target (on a seat surface or a seat back portion) and a load at a threshold value or more is detected, where a seat belt is worn, or where an ignition key (for the driver's seat) is turned on, it is determined that the passenger is seated.

(2) Timing 2

A start button is disposed in the pulse wave detection devices 1, and when any one of the passengers selects the start button, the processing is started.

The start button in this case is constituted by the display unit 5 and the input unit 6. That is, the pulse wave detection device 1 displays an image of the start button on the display unit 5 and starts the processing when the touch panel of the input unit 6 detects a fact that the portion is touched.

Moreover, an independent hard switch may be provided as the input unit 6.

It is to be noted that the start button may be provided for each of the passengers to be monitored.

(3) Timing 3

When a door of the driver's seat of a vehicle on which the pulse wave detection device 1 is mounted is opened, the processing is started.

It is to be noted that, when the passenger other than the driver is also a monitoring target, the processing is started also when the door corresponding to the applicable passenger is opened.

The opening/closing of the door is detected by a known technology such as an opening/closing sensor (touch sensor) on a door portion or the like.

According to this timing 3, the monitoring of the pulse wave can be started as early as possible as compared with the other timings.

Particularly, since the processing before the pulse wave detection processing (Step 35) such as obtaining of the skin color data can be completed after the door is opened and until the passenger is seated, and the pulse wave can be detected for a longer time.

Subsequently, a usage method of the detected pulse wave will be explained. That is, by using the pulse wave detected by the pulse wave detection device 1 of this embodiment, a state of the driver including sleepiness, tensed state, awakened state such as fatigue and the like can be determined and coped with.

Technologies for detecting sleepiness of the driver from the pulse wave, for example, include a "sleepiness predicting device and sleepiness prediction system" in Japanese Patent No. JP2014-20678A. By using this technology as an example, presence of sleepiness can be monitored from the pulse wave of the driver.

In detail, by using the pulse wave detected by the pulse wave detection device 1, a pulse and HF of the driver are measured. The HF is a known index indicating a fluctuation amount of heartbeat intervals (fluctuation in a heart rate).

The sleepiness of the driver can be calculated by the following sleepiness numerical value Z.

$$Z = P \times 10 + (Q-1) \times 100$$

Reference character P denotes a drop amount of the pulse with respect to a value at a normal time (simply referred to as bpm), and reference character Q denotes an increase rate of the HF in a predetermined period (past 500 seconds, for example).

In a state with a sign of sleepiness, since sympathetic nervous system activities change from an enhanced state to a suppressed state, the pulse rate lowers. In a state where sleepiness occurs, since parasympathetic nervous system changes to the enhanced state, the pulse rate lowers, while the HF rises.

The pulse wave detection device 1 monitors the pulse wave, the pulse acquired from the pulse wave, the HF, the sleepiness numerical value z and the like and outputs vibration or sound when the sign of sleepiness is found or the sleepiness occurs, which can call an attention of the driver.

Moreover, since the pulse also changes in accordance with the tensed state, fatigue and the like in addition to the sleepiness, the pulse wave detection device 1 can also monitor the awakened state of the driver including these concepts by the pulse wave.

The three embodiments have been explained above, but according to the first embodiment, the following configuration can be obtained.

(1) 101-st Configuration

A pulse wave detection device comprising moving image obtaining means for obtaining a moving image taking a region including at least skin of a target, skin portion specifying means for specifying a skin portion of the target shown on the obtained moving image, pulse wave obtaining means for obtaining a pulse wave of the target from a temporal change of predetermined color space components in the skin portion specified as above, and output means for outputting the obtained pulse wave.

(2) 102-nd Configuration

The pulse wave detection device of the 101-st configuration, wherein the region including at least the skin of the target includes the face of the target.

(3) 103-rd Configuration

The pulse wave detection device of the 101-st or the 102-nd configuration, further comprising reference component registering means for registering a reference component which is the color space component to be a reference for specifying the skin portion of the target, wherein the skin portion specifying means specifies a portion where the predetermined color space component corresponds to the registered reference component in the moving image as the skin portion.

(4) 104-th Configuration

The pulse wave detection device of the 101-st, the 102-nd or the 103-rd configuration, wherein the color space component used by the skin portion specifying means for specifying the skin portion and the color space component used by the pulse wave obtaining means for obtaining the pulse wave are different color space components.

(5) 105-th Configuration

The pulse wave detection device of the 104-th configuration, wherein the color space component used by the skin portion specifying means for specifying the skin portion is a hue component (H) of an HSV color space made of the hue component (H), a saturation component (S), and a brightness component (V), and the color space component used by the pulse wave obtaining means for obtaining the pulse wave is a chromaticity component (Q) in a YIQ color space made of a brightness component (Y) and chromaticity components (I, Q).

(6) 106-th Configuration

The pulse wave detection device of any one of the 101-st to the 104-th configurations further comprising color space converting means for converting a color space of the moving image, wherein the skin portion specifying means and the pulse wave obtaining means obtain a color space component in the color space obtained by converting the obtained moving image by the color space converting means.

(7) 107-th Configuration

The pulse wave detection device of the 103-rd configuration, further comprising face image obtaining means for obtaining a face image taking a face of the target, and region specifying means for specifying a predetermined region where skin of the face is exposed by face recognition processing in the obtained face image, wherein the reference component registering means registers the color space component of the specified region as the reference component.

(8) 108-th Configuration

The pulse wave detection device of the 107-th configuration, wherein the predetermined region is a nose region of the target.

(9) 109-th Configuration

The pulse wave detection device of the 107-th or the 108-th configuration, wherein the reference component registering means registers a value obtained by applying statistical processing to distribution of the color space component in the specified region.

(10) 110-th Configuration

The pulse wave detection device of any one of the 101-st to the 109-th configurations, wherein the skin portion specifying means specifies the skin portion by the pixel values of the moving image.

(11) 111-th Configuration

The pulse wave detection device of any one of the 101-st to the 109-th configurations, wherein the target is a passenger of transportation equipment and monitoring means for monitoring a physical condition of the passenger by using the output pulse wave is provided.

(12) 112-th Configuration

A pulse wave detection program for realizing by a computer, a moving image obtaining function for obtaining a moving image taking a region including at least skin of a target, a skin portion specifying function for specifying a skin portion of the target shown on the obtained moving image, a pulse wave obtaining function for obtaining a pulse wave of the target from a temporal change of the color space components in the specified skin portion; and an outputting function for outputting the obtained pulse wave.

By means of the configuration described above, the following effects can be obtained.

(1) According to the 101-st configuration, accuracy of pulse wave detection can be improved since a disturbance element shown on a moving image is excluded and only a skin portion is taken out, a pulse wave can be detected therefrom.

(2) According to the 102-nd configuration, the pulse wave can be detected from the face which can be photographed easily since the skin is usually exposed.

(3) According to the 103-rd configuration, the skin portion can be easily extracted by comparison with a reference component.

(4) According to the 104-th configuration, by employing a combination of color space components suitable for an observation target (since a target observed by light is different between the skin and the pulse wave), robustness against the disturbance element can be improved.

(5) According to the 105-th configuration, by combining an H component found to be suitable in specification of the skin portion and a Q component found to be suitable for pulse wave detection, robustness against the disturbance element can be improved.

(6) According to the 106-th configuration, by including color space conversion processing not in an external device but inside a pulse wave detection device, processing speed is improved, and the pulse wave can be detected from the moving image easily on a real time basis.

(7) According to the 107-th configuration, by sampling a reference component of a color of the skin from the target himself/herself, a reference value including a subtle difference in skin color depending on a person can be easily obtained.

(8) According to the 108-th configuration, the reference value of the color of the skin can be sampled from a region of a nose where the skin is exposed and spot specification is easy.

(9) According to the 109-th configuration, biased distribution of the color of skin with a large individual difference can be averaged by statistical processing, whereby reliability of a reference component can be improved.

(10) According to the 110-th configuration, a pixel acting as the disturbance element can be excluded from the evaluation target since the skin portion is extracted not from a region surrounded by a closed curve (where pixels not applicable to the skin portion are also scattered) but by the pixel values, whereby detection accuracy can be improved.

(11) According to the 111-th configuration, a physical condition of a passenger onboard transportation equipment can be monitored.

(12) According to the 112-th configuration, by spreading a pulse wave detection program and by installing it in a general-purpose computer, a pulse wave detection device can be configured easily and inexpensively.

Moreover, according to the third embodiment, the following configuration can be obtained.

(1) 301-st Configuration

A pulse wave detection device comprising moving image obtaining means for obtaining a moving image taking a region including at least skin of a target by a predetermined camera, skin portion specifying means for specifying a skin portion of the target shown on the obtained moving image, fluctuation correcting means for correcting fluctuation in predetermined color space components generated in the moving image caused by characteristics of the camera, pulse wave obtaining means for obtaining a pulse wave of the target from a temporal change of the color space components in the skin portion thus corrected, and output means for outputting the obtained pulse wave.

(2) 302-nd Configuration

The pulse wave detection device of the 301-st configuration characterized in that the region including at least the skin of the target includes the face of the target.

(3) 303-rd Configuration

The pulse wave detection device of the 302-nd configuration further comprising update means for updating a correction value used for the correction by applying predetermined statistical processing to a change in the color space components generated in the skin portion with movement of the face.

(4) 304-th Configuration

The pulse wave detection device of the 303-rd configuration characterized in that the update means updates the correction value for each pixel constituting the moving image, and the fluctuation correcting means corrects the color space components by a correction value corresponding to the pixel for each of the pixels.

(5) 305-th Configuration

The pulse wave detection device of the 303-rd or the 304-th configuration characterized in that the update means completes the update when the size of fluctuation in the color space components caused by the camera characteristics converges to at least a value smaller than the size of a change in the color space components.

(6) 306-th Configuration

The pulse wave detection device of the 303-rd, the 304-th or the 305-th configuration characterized in that the fluctuation correcting means corrects the fluctuation by using the latest correction value while the update means updates the correction value, and the pulse wave obtaining means obtains the pulse wave form the skin portion corrected by the latest correction value.

(7) 307-th Configuration The pulse wave detection device of any one of the 301-st to the 306-th configurations further comprising brightness change obtaining means for obtaining a change in brightness generated by a change in a photographing environment of the moving image, and brightness correcting means for correcting the brightness of the moving image by using the obtained change in the brightness, characterized in that the pulse wave obtaining means obtains a pulse wave of the target from a temporal change in the color space components in the skin portion further corrected by the brightness correcting means.

(8) 308-th Configuration

The pulse wave detection device of any one of the 301-st to the 307-th configurations characterized in that the color space component to be corrected by the fluctuation correcting means and the color space component used by the pulse wave obtaining means for obtaining the pulse wave are a chromaticity component (Q) of a YIQ color space made of a brightness component (Y) and chromaticity components (I, Q).

(9) 309-th Configuration

The pulse wave detection device of any one of the 301-st to the 308-th configurations characterized in that the target is a passenger of transportation equipment and monitoring means for monitoring a physical condition of the passenger by using the output pulse wave.

(10) 310-th Configuration A pulse wave detection program for realizing by a computer a moving image obtaining function for obtaining a moving image taking a region including at least skin of a target by a predetermined camera, a skin portion specifying function for specifying a skin portion of the target shown on the obtained moving image, a fluctuation correcting function for correcting fluctuation in predetermined color space components generated in the moving image caused by characteristics of the camera, a pulse wave obtaining function for obtaining a pulse wave of the target from a temporal change of the color space components in the skin portion thus corrected, and an outputting function for outputting the obtained pulse wave.

By means of the configuration described above, the following effects can be obtained.

(1) According to the 301-st configuration, by correcting the fluctuation in the predetermined color space components generated in the moving image caused by the camera characteristics, the pulse wave can be favorably detected.

(2) According to the 302-nd configuration, the pulse wave can be detected from the face which can be photographed easily since the skin is usually exposed.

(3) According to the 303-rd configuration, the correction value is updated by a change in the color space component generated by movement of the face, and at that time, fluctuation in the correction value can be averaged by statistical processing.

(4) According to the 304-th configuration, by correcting the region not by a representative value but for each pixel, correction accuracy can be improved.

(5) According to the 305-th configuration, by converging the correction until the fluctuation in the color space components becomes smaller than the fluctuation in the pulse wave, the pulse wave can be detected favorably.

(6) According to the 306-th configuration, the pulse wave can be detected while correction is made.

(7) According to the 307-th configuration, by further correcting the brightness of the moving image, robustness against an environmental change is improved, and the pulse wave can be detected even in the brightness changes.

(8) According to the 308-th configuration, by setting the color space component for pulse wave detection to the Q component found to be suitable for the pulse wave detection, robustness against disturbance elements can be improved.

(9) According to the 309-th configuration, a physical condition of the passenger of transportation equipment can be monitored.

(10) According to the 310-th configuration, by distributing a pulse wave detection program and by installing it in a general-purpose computer, a pulse wave detection device can be configured easily and inexpensively.

EXPLANATIONS OF LETTERS OR NUMERALS 1 pulse wave detection device
2 CPU
3 ROM
4 RAM
5 display unit
6 input unit
7 output unit
8 camera
9 storage unit
10 user
12 pulse wave detection program
14 user database
15 camera characteristic data
20 nose region
21 hair
22 eyebrow
23 eye
24 lip
25 background
26 skin portion
30 still image
31 frame image
32 HSV image
35 pulse wave
41, 42 period
45 eye portion
46 white eye portion
47 iris portion
48 pupil portion
51 brightness signal
52 before correction pulse wave signal
53 after correction pulse wave signal
55 eye region
61 left region
62 center region
63 right region
101 evaluation region
102 background

The invention claimed is:

1. A pulse wave detection device comprising:
moving image obtaining means for obtaining a moving image photographing a region including a face of a target;
eye portion specifying means for specifying an eye portion of the target shown on the moving image;
brightness change obtaining means for obtaining a change in brightness caused by a change in a photographing environment of the moving image, by detecting a change in a predetermined color space component of the specified eye portion;
brightness correcting means for correcting the brightness of a skin portion of the target in a frame image of the moving image, or correcting the brightness of the entire frame image, using the change in the brightness obtained by the detecting of the change in the predetermined color space component of the specified eye portion;
pulse wave obtaining means for obtaining a pulse wave of the skin portion from a temporal change in the predetermined color space component in the skin portion after the brightness of the skin portion or of the entire frame image is corrected as above, the pulse wave being a wave travelling through the skin portion; and output means for outputting the obtained pulse wave.

2. The pulse wave detection device according to claim 1, further comprising:

skin portion specifying means for specifying the skin portion of the target shown on the obtained moving image, wherein the pulse wave obtaining means obtains a pulse wave of the target from the temporal change of the predetermined color space component on the specified skin portion.

3. The pulse wave detection device according to claim 2, further comprising:

reference component registration means for registering a reference component which is a color space component to be a reference for specifying the eye portion of the target, wherein the eye portion specifying portion specifies a portion where the predetermined color space component corresponds to the registered reference component in the moving image as the eye portion.

4. The pulse wave detection device according to claim 2, wherein the skin portion specifying means specifies a portion where the predetermined color space component corresponds to the registered reference component in the moving image as the skin portion.

5. The pulse wave detection device according to claim 2, wherein the color space component used by the brightness change obtaining means for obtaining the change in brightness, the color space component used by the pulse wave obtaining means for obtaining the pulse wave, and the color space component used by the skin portion specifying means for specifying the skin portion are different color space components.

6. The pulse wave detection device according to claim 5, wherein the color space component used by the brightness change obtaining means for obtaining the change in brightness and the color space component used by the pulse wave obtaining means for obtaining the pulse wave are a brightness component (Y) and a chromaticity component (Q) of a YIQ color space made of the brightness component (Y) and the chromaticity components (I, Q), respectively; and the color space component used by the skin portion specifying means for specifying the skin portion is a hue component (H) of an HSV color space made of the hue component (H), a saturation component (S), and a brightness component (V).

7. The pulse wave detection device according to claim 2, further comprising:

color space converting means for converting a color space, wherein the pulse wave obtaining means, the brightness change obtaining means, and the skin portion specifying means obtain a color space component in the color space obtained by converting the obtained moving image by the color space converting means.

8. The pulse wave detection device according to claim 3, further comprising:

face image obtaining means for obtaining a face image obtained by photographing the face of the target; and region specifying means for specifying a region of the eye in the face by face recognition processing in the obtained face image, wherein the reference component registration means registers a color space component in the specified region as the reference component.

9. The pulse wave detection device according to claim 8, wherein the reference component registration means registers a value obtained by applying predetermined statistical processing to distribution of a color space component in the specified region as the reference component.

10. The pulse wave detection device according to claim 1, wherein the eye portion specifying means specifies the eye portion by the pixel values of the moving image.

11. The pulse wave detection device according to claim 1, wherein the brightness correcting means executes the correction by the pixel values of the moving image.

12. The pulse wave detection device according to claim 1, wherein the target is a passenger of transportation equipment, and monitoring means for monitoring a physical condition of the passenger by using the output pulse is provided.

13. A non-transitory computer readable medium storing thereon a pulse wave detection program for realizing by a computer:

a moving image obtaining function of obtaining a moving image photographing a region including a face of a target;

an eye portion specifying function of specifying an eye portion of the target shown on the moving image;

a brightness change obtaining function of obtaining a change in brightness caused by a change in a photographing environment of the moving image, by detecting a change in a predetermined color space component of the specified eye portion;

a brightness correcting function of correcting the brightness of a skin portion of the target in a frame image of the moving image, or correcting the brightness of the entire frame image, using the change in the brightness obtained by the detecting of the change in the predetermined color space component of the specified eye portion;

a pulse wave obtaining function of obtaining a pulse wave of the skin portion from a temporal change in the predetermined color space component in the skin portion after the brightness of the skin portion or of the entire frame image is corrected as above, the pulse wave being a wave travelling through the skin portion; and an output function of outputting the obtained pulse wave.

* * * * *